US012569525B2

(12) United States Patent
Wilson et al.

(10) Patent No.: US 12,569,525 B2
(45) Date of Patent: *Mar. 10, 2026

(54) GENE THERAPY FOR TREATING PHENYLKETONURIA

(71) Applicant: The Trustees of the University of Pennsylvania, Philadelphia, PA (US)

(72) Inventors: James M. Wilson, Philadelphia, PA (US); Jenny Agnes Sidrane, Phoenixville, PA (US); Scott Ashley, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 497 days.

This patent is subject to a terminal disclaimer.

(21) Appl. No.: 17/832,961

(22) Filed: Jun. 6, 2022

(65) Prior Publication Data

US 2022/0313760 A1      Oct. 6, 2022

Related U.S. Application Data

(63) Continuation of application No. 16/474,960, filed as application No. PCT/US2017/068897 on Dec. 29, 2017, now Pat. No. 11,382,941.

(60) Provisional application No. 62/440,651, filed on Dec. 30, 2016, provisional application No. 62/469,898, filed on Mar. 10, 2017, provisional application No. 62/505,373, filed on May 12, 2017.

(51) Int. Cl.
| | |
|---|---|
| *A61K 35/761* | (2015.01) |
| *A61K 48/00* | (2006.01) |
| *A61P 3/00* | (2006.01) |
| *C12N 15/52* | (2006.01) |
| *C12N 15/86* | (2006.01) |

(52) U.S. Cl.
CPC ........ *A61K 35/761* (2013.01); *A61K 48/0075* (2013.01); *A61K 48/0083* (2013.01); *A61P 3/00* (2018.01); *C12N 15/52* (2013.01); *C12N 15/86* (2013.01); *C12Y 114/16001* (2013.01)

(58) Field of Classification Search
None
See application file for complete search history.

(56) References Cited

U.S. PATENT DOCUMENTS

| | | | | |
|---|---|---|---|---|
| 6,069,133 A | * | 5/2000 | Chiou ................ | A61K 48/0066 |
| | | | | 424/85.4 |
| 8,999,380 B2 | | 4/2015 | Bancel et al. | |
| 10,308,958 B2 | | 6/2019 | Gao et al. | |
| 11,555,059 B2 | * | 1/2023 | Wilson ..................... | C12N 7/00 |
| 11,832,941 B2 | * | 12/2023 | Zhang .................. | A61B 5/6821 |
| 2004/0142416 A1 | | 7/2004 | Lapis et al. | |
| 2006/0136184 A1 | | 6/2006 | Gustafsson et al. | |
| 2014/0032186 A1 | | 1/2014 | Gustafsson et al. | |

| | | | |
|---|---|---|---|
| 2015/0110858 A1 | | 4/2015 | Derosa et al. |
| 2015/0315612 A1 | | 11/2015 | Wilson et al. |
| 2019/0002844 A1 | | 1/2019 | Lock et al. |

FOREIGN PATENT DOCUMENTS

| | | | | |
|---|---|---|---|---|
| EP | 2180058 A1 | * | 4/2010 | ............. C12N 15/85 |
| WO | WO 2003/052051 | | 6/2003 | |
| WO | WO 2014/151341 A1 | | 6/2003 | |
| WO | WO 2005/033321 | | 4/2005 | |
| WO | WO 2011/126808 | | 10/2011 | |
| WO | WO 2013/049493 | | 4/2013 | |
| WO | WO-2013173129 A2 | * | 11/2013 | ............. A61B 3/032 |
| WO | WO 2014/151341 | | 9/2014 | |
| WO | WO 2015/061491 | | 10/2014 | |
| WO | WO 2015/012924 | | 1/2015 | |
| WO | WO 2015/138348 A1 | | 9/2015 | |

OTHER PUBLICATIONS

Sun, et al. (2006) "Enhanced Efficacy of an AAV Vector Encoding Chimeric Highly Secreted Acid [alpha]-Glucosidase in Glycogen Storage Disease Type II", Molecular Therapy, 14(6): 822-30. (Year: 2006).*
Oh, et al. (2004) "Long-Term Enzymatic and Phenotypic Correction in the Phenylketonuria Mouse Model by Adeno-Associated Virus Vector Mediated Gene Transfer", Pediatric Research, 56: 278-84. (Year: 2004).*
Inagaki, et al. (2006) "Robust systemic transduction of with AAV9 vectors in mice: efficient global cardiac gene transfer superior to AAV8", Molecular Therapy, 14(1): 45-53. (Year: 2006).*
McIntosh, J et al. Therapeutic levels of FVIII following a single peripheral vein administration of rAAV vector encoding a novel human factor VIII variant. Blood. Apr. 25, 2013;121(17):3335-44.
NCBI GenBank Accession No. BC026251, PAH phenylalanine hydroxylase [*Homo sapiens* (human)], Jul. 15, 2006.
Office Action dated Feb. 21, 2023 issued in corresponding Korean Patent Application No. 10-2019-7021767, with English translation provided by local agent.
Al Hafid, et al., Phenylketonuria: a review of current and future treatments, Translational Pediatrics, vol. 4(4):304-317, Oct. 2015.
Almond et al., A Comparison of pCI-neo Vector and pcDNA4/HisMax Vector. American Medical Association, 7(10):1-9, 2000.
Calcedo et al., Worldwide Epidemiology of Neutralizing Antibodies to Adeno-Associated Viruses, The Journal of Infectious Diseases, vol. 199(3)1-10, Feb. 2009.
Chuah et al., Liver-specific transcriptional modules identified by genome-wide in silico analysis enable efficient gene therapy in mice and non-human primates, Mol Ther. Sep. 2014;22(9):1605-13.
Conlon et al., Efficient hepatic delivery and expression from a recombinant adeno-associated virus 8 pseudotyped alpha1-antitrypsin vector, Mol Ther. Nov. 2005;12(5):867-75.

(Continued)

*Primary Examiner* — Robert M Kelly
(74) *Attorney, Agent, or Firm* — Howson & Howson LLP; Colleen M. Schaller

(57) ABSTRACT

Compositions and regimens useful in treating phenylketonuria are provided. The compositions include recombinant adeno-associated virus (rAAV) with a transthyretin enhancer and promoter driving expression of a human phenylalanine hydroxylase.

19 Claims, 12 Drawing Sheets

Specification includes a Sequence Listing.

(56)        References Cited

OTHER PUBLICATIONS

Ding et al., Administration-route and gender-independent long-term therapeutic correction of phenylketonuria (PKU) in a mouse model by recombinant adeno-associated virus 8 pseudotyped vector-mediated gene transfer, Gene Therapy, vol. 13(7):587-593, Apr. 2006.

Gao et al., Adeno-associated viruses undergo substantial evolution in primates during natural infections, Proceedings of the National Academy of Sciences of the U.S.A., vol. 100(10):6081-6086, May 2003.

Gregory et al., Blood phenylalanine monitoring for dietary compliance among patients with phenylketonuria: comparison of methods, Genet Med 9(11):761-765, Nov. 2007.

Grieger et al., Packaging capacity of adeno-associated virus serotypes: impact of larger genomes on infectivity and postentry steps, J Virol. Aug. 2005;79(15):9933-44.

Grimm et al., Titration of AAV-2 particles via a novel capsid ELISA: packaging of genomes can limit production of recombinant AAV-2, Gene Therapy, vol. 6(7):1322-1330, Jul. 1999.

Harding et al., Complete correction of hyperphenylalaninemia following liver-directed, recombinant AAV2/8 vector-mediated gene therapy in murine phenylketonuria, Gene Therapy, vol. 13(5):457-62, Mar. 2006.

Harding et al., Intravenous administration of an AAV-2 vector for the expression of factor IX in mice and a dog model of hemophilia B, Gene Ther. Jan. 2004;11(2):204-13.

Kaufman, A model of human phenylalanine metabolism in normal subjects and in phenylketonuric patients, Proceedings of the National Academy of Sciences of the United States of America, vol. 96(6):3160-4, Mar. 1999.

Kelly et al., Splicing of many human genes involves sites embedded within introns, Nucleic Acids Research, vol. 43(9):4721-4732, May 2015.

Lock, et al., Absolute determination of single-stranded and self-complementary adeno-associated viral vector genome titers by droplet digital PCR, Human Gene Therapy Methods, vol. 25(2):115-25, Apr. 2014.

Lock, et al., Rapid, simple, and versatile manufacturing of recombinant adeno-associated viral vectors at scale, Human Gene Therapy, vol. 21(10):1259-71, Oct. 2010.

McClements et al., Gene therapy for retinal disease, Transl Res Apr. 2013;161(4):241-54.

Miao et al., Inclusion of the hepatic locus control region, an intron, and untranslated region increases and stabilizes hepatic factor IX gene expression in vivo but not in vitro, Mol Ther. Jun. 2000;1(6):522-32.

Miyatake, et al., Transcriptional targeting of herpes simplex virus for cell-specific replication, Journal of Virology, vol. 71(7):5124-5132, Mar. 1997.

Mizukami, et al., A Protocol for AAV vector production and purification. Diss. Division of Genetic Therapeutics, Center for Molecular Medicine, 1998.

Sandig, et al., HBV-derived promoter's direct liver-specific expression of an adenovirally transduced LDL receptor gene, Gene therapy, vol. 3(11):1002-9, Nov. 1996.

Shepelev, et al., Advances in the Exon-Intron Database (EID), Briefings in Bioinformatics, vol. 7(2):178-785, Jun. 2006.

Thompson, et al., A comprehensive comparison of multiple sequence alignment programs, Nucleic acids research, vol. 27(13):2682-2690, May 1999.

Viecelli et al., Treatment of phenylketonuria using minicircle-based naked-DNA gene transfer to murine liver, Hepatology, vol. 60(3):1035-43, Jul. 2014.

Wobus, et al., Monoclonal antibodies against the adeno-associated virus type 2 (AAV-2) capsid: epitope mapping and identification of capsid domains involved in AAV-2-cell interaction and neutralization of AAV-2 infection, Journal of Virology, vol. 74(19):9281-93, Oct. 2000.

Wu, et al., Effect of genome size on AAV vector packaging, Molecular therapy: The Journal of the American Society of Gene Therapy, vol. 18(1):80-6, Jan. 2010.

Wu, et al., Optimization of Self-complementary AAV Vectors for Liver-directed Expression Results in Sustained Correction of Hemophilia B at Low Vector Dose, The American Society of Gene Therapy, vol. 16(2):280-289, Feb. 2008.

Yagi et al., Complete restoration of phenylalanine oxidation in phenylketonuria mouse by a self-complementary adeno-associated virus vector, The Journal of Gene Medicine, vol. 13(2):114-122, Feb. 2011.

Yan et al., Human thyroxine binding globulin (TBG) promoter directs efficient and sustaining transgene expression in liver-specific pattern, Gene. Sep. 15, 2012;506(2):289-94.

International Search Report and Written Opinion Issued on the International Patent Application No. PCT/US2017/068897, dated Nov. 11, 2018.

Supplementary European Search Report and Opinion issued in European Patent Application No. 17887983, dated Jul. 17, 2020.

Office Action issued in Japanese Patent Application No. 2019-53581, dated Dec. 8, 2021, with unofficial English translation provided by local agent.

Office Action issued in Japanese Patent Application No. 2019-53581, dated Jul. 6, 2022, with unofficial English translation provided by local agent.

Office Action issued in Chinese Patent Application No. 201780087369.2, issued Jul. 22, 2022, with unofficial English translation provided by local agent.

Non-Final Office Action in U.S. Appl. No. 16/474,960, dated Dec. 17, 2021.

Applicant's Amendment and Response in U.S. Appl. No. 16/474,960, filed Mar. 16, 2022.

Notice of Allowance in U.S. Appl. No. 16/474,960, mailed Apr. 6, 2022.

* cited by examiner

FIG. 1

→ 1E12 GC/kg TBG.PAH.BGH
→ 1E12 GC/kg TBG.PAH.WPRE.BGH
→ PBS

FIG 8A
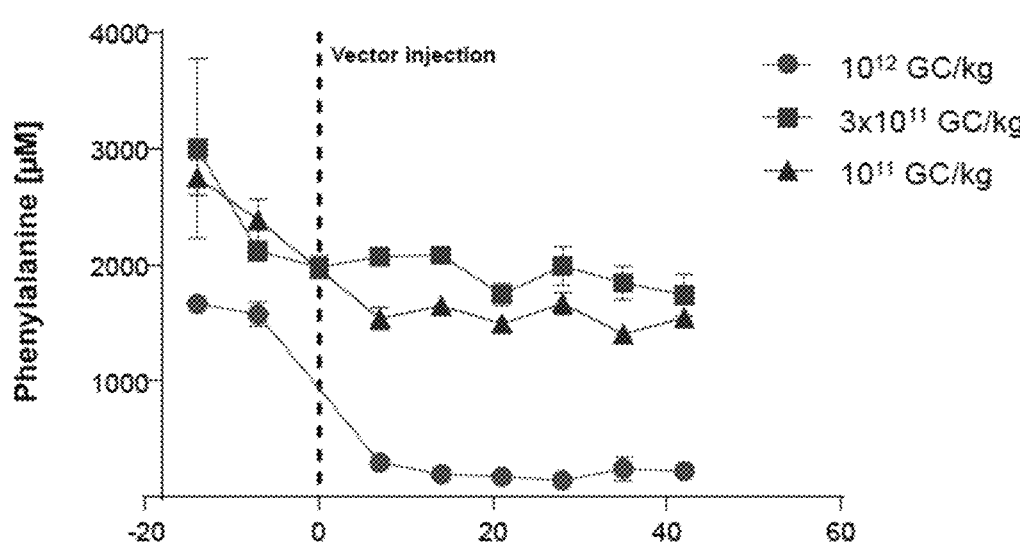
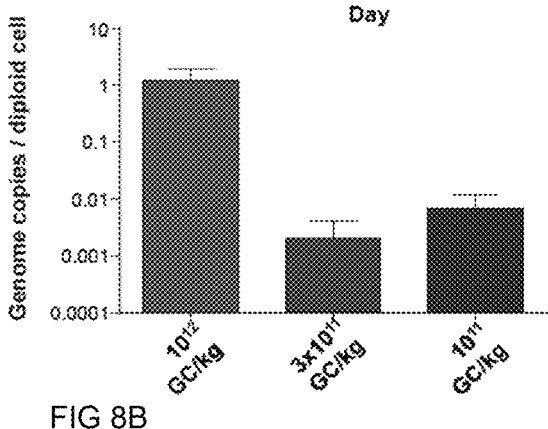
FIG 8B
FIG 8C
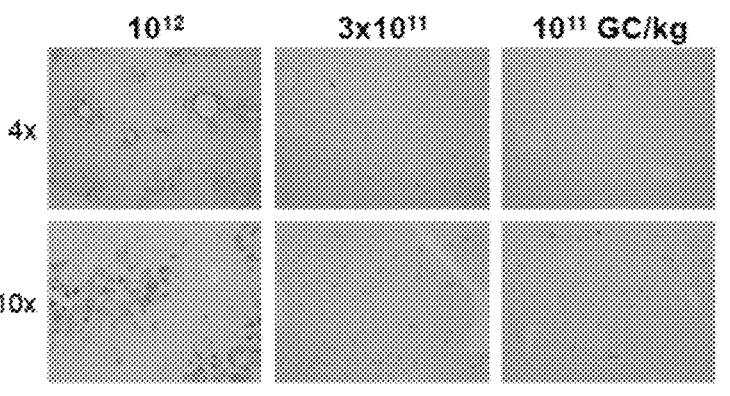

SEQUENCE LISTING

<160> NUMBER OF SEQ ID NOS: 31

<210> SEQ ID NO 1
<211> LENGTH: 1356
<212> TYPE: DNA
<213> ORGANISM: Artificial Sequence
<220> FEATURE:
<223> OTHER INFORMATION: constructed sequence

<400> SEQUENCE: 1
atgtctaccg ccgtgctgga aaatcccggc ctgggcagaa agctgagcga cttcggccag      60
gaaaccagct acatcgagga caactgcaac cagaacggcg ccatcagcct gatcttcagc     120
ctgaaagaag aagtgggcgc cctggccaag gtgctgcggc tgttcgaaga gaacgacgtg     180
aacctgaccc acatcgagag ccggcccagc agactgaaga aggacgagta cgagttcttc     240
acccacctgg acaagcggag cctgcccgcc ctgaccaaca tcatcaagat cctgcggcac     300
gacatcggcg ccaccgtgca cgagctgagc cgggacaaga aaaaggacac cgtgccctgg     360
ttcccccgga ccatccagga actggacaga ttcgccaacc agatcctgag ctacggcgcc     420
gagctggacg ccgatcaccc cggctttaag gaccccgtgt accgggccag acggaagcag     480
tttgccgata tcgcctacaa ctaccggcac ggccagccca tcccccgggt ggagtatatg     540
gaagaggaaa agaaaacctg gggcaccgtg ttcaagaccc tgaagtccct gtacaagacc     600
cacgcctgct acgagtacaa ccacatcttc ccactgctgg aaaagtactg cggcttccac     660
gaggacaata tcccccagct ggaagacgtg tcccagttcc tgcagacctg caccggcttc     720
agactgaggc ctgtggccgg actgctgagc agcagagatt ttctgggcgg actggccttc     780
cgggtgttcc actgcacccca gtacatcaga cacggcagca gcccatgta cacccccgag     840 cccgatatct gccacgagct gctgggacac gtgcccctgt tcagcgacag aagcttcgcc     900
cagttcagcc aggaaatcgg cctggcctct ctgggagccc ccgacgagta tatcgagaag     960
ctggccacca tctactggtt caccgtggaa ttcggcctgt gcaagcaggg cgacagcatc    1020
aaggcctacg gcgctggcct gctgtccagc tttggcgagc tgcagtactg tctgagcgag    1080
aagcccaagc tgctgcccct ggaactggaa aagaccgcca tccagaacta caccgtgacc    1140
gagttccagc ccctgtacta cgtggccgag agcttcaacg acgccaaaga aaaagtgcgg    1200
aacttcgccg ccaccatccc cagaccattc tccgtcagat acgacccccta cacccagcgg    1260 atcgaggtgc tggacaacac acagcagctg aaaattctgg ccgactccat caacagcgag    1320
atcggcatcc tgtgcagcgc cctgcagaag atcaag                            1356

<210> SEQ ID NO 2
<211> LENGTH: 452
<212> TYPE: PRT
<213> ORGANISM: Homo sapiens

<400> SEQUENCE: 2

Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
            20                  25                  30

Gly Ala Ile Ser Leu Ile Phe Ser Leu Lys Glu Glu Val Gly Ala Leu
        35                  40                  45

-continued

```
Ala Lys Val Leu Arg Leu Phe Glu Glu Asn Asp Val Asn Leu Thr His
    50                  55                  60

Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
            85                  90                  95

Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
            115                 120                 125

Asp Arg Phe Ala Asn Gln Ile Leu Ser Tyr Gly Ala Glu Leu Asp Ala
    130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Glu Lys Lys Thr Trp Gly Thr Val Phe Lys
            180                 185                 190

Thr Leu Lys Ser Leu Tyr Lys Thr His Ala Cys Tyr Glu Tyr Asn His
            195                 200                 205

Ile Phe Pro Leu Leu Glu Lys Tyr Cys Gly Phe His Glu Asp Asn Ile
    210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
                260                 265                 270

Ser Lys Pro Met Tyr Thr Pro Glu Pro Asp Ile Cys His Glu Leu Leu
            275                 280                 285

Gly His Val Pro Leu Phe Ser Asp Arg Ser Phe Ala Gln Phe Ser Gln
    290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Glu Lys Pro Lys Leu Leu Pro Leu Glu
            355                 360                 365

Leu Glu Lys Thr Ala Ile Gln Asn Tyr Thr Val Thr Glu Phe Gln Pro
    370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
            420                 425                 430

Leu Ala Asp Ser Ile Asn Ser Glu Ile Gly Ile Leu Cys Ser Ala Leu
            435                 440                 445

Gln Lys Ile Lys
    450
```

<210> SEQ ID NO 3
<211> LENGTH: 1359
<212> TYPE: DNA
<213> ORGANISM: Homo sapiens

<400> SEQUENCE: 3
atgtccactg cggtcctgga aaacccaggc ttgggcagga aactctctga ctttggacag      60
gaaacaagct atattgaaga caactgcaat caaaatggtg ccatatcact gatcttctca     120
ctcaaagaag aagttggtgc attggccaaa gtattgcgct tatttgagga gaatgatgta     180
aacctgaccc acattgaatc tagaccttct cgtttaaaga aagatgagta tgaatttttc     240
acccatttgg ataaacgtag cctgcctgct ctgacaaaca tcatcaagat cttgaggcat     300
gacattggtg ccactgtcca tgagctttca cgagataaga agaaagacac agtgccctgg     360
ttcccaagaa ccattcaaga gctggacaga tttgccaatc agattctcag ctatggagcg     420
gaactggatg ctgaccaccc tggttttaaa gatcctgtgt accgtgcaag acggaagcag     480
tttgctgaca ttgcctacaa ctaccgccat gggcagccca tccctcgagt ggaatacatg     540
gaggaagaaa agaaaacatg gggcacagtg ttcaagactc tgaagtcctt gtataaaacc     600
catgcttgct atgagtacaa tcacattttt ccacttcttg aaaagtactg tggcttccat     660
gaagataaca ttccccagct ggaagacgtt tctcaattcc tgcagacttg cactggtttc     720
cgcctccgac ctgtggctgg cctgctttcc tctcgggatt tcttgggtgg cctggccttc     780
cgagtcttcc actgcacaca gtacatcaga catggatcca agcccatgta taccccgaa     840 cctgacatct gccatgagct gttgggacat gtgcccttgt tttcagatcg cagctttgcc     900 cagtttttccc aggaaattgg ccttgcctct ctgggtgcac ctgatgaata cattgaaaag     960
ctcgccacaa tttactggtt tactgtggag tttgggctct gcaaacaagg agactccata    1020
aaggcatatg gtgctgggct cctgtcatcc tttggtgaat acagtactg cttatcagag    1080 aagccaaagc ttctcccct ggagctggag aagacagcca tccaaaatta cactgtcacg    1140
gagttccagc ccctgtatta cgtggcagag agtttttaatg atgccaagga gaaagtaagg    1200
aactttgctg ccacaatacc tcggcccttc tcagttcgct acgacccata cacccaaagg    1260
attgaggtct tggacaatac ccagcagctt aagatttttgg ctgattccat taacagtgaa    1320
attggaatcc tttgcagtgc cctccagaaa ataaagtaa                            1359

<210> SEQ ID NO 4
<211> LENGTH: 34
<212> TYPE: DNA
<213> ORGANISM: Artificial Sequence
<220> FEATURE:
<223> OTHER INFORMATION: constructed sequence

<400> SEQUENCE: 4
tgtttgctgc ttgcaatgtt tgcccatttt aggg                                    34

<210> SEQ ID NO 5
<211> LENGTH: 100
<212> TYPE: DNA
<213> ORGANISM: Artificial Sequence
<220> FEATURE:
<223> OTHER INFORMATION: constructed sequence

<400> SEQUENCE: 5
ctacctcgtg atcgcccggc ccctgttcaa acatgtccta atactctgtc tctgcaaggg      60
tcatcagtag ttttccatct tactcaacat cctcccagtg                             100

```
<210> SEQ ID NO 6
<211> LENGTH: 42
<212> TYPE: DNA
<213> ORGANISM: Artificial Sequence
<220> FEATURE:
<223> OTHER INFORMATION: constructed sequence

<400> SEQUENCE: 6
aggttaattt ttaaactgtt tgctctggtt aataatctca gg                            42

<210> SEQ ID NO 7
<211> LENGTH: 322
<212> TYPE: DNA
<213> ORGANISM: Artificial Sequence
<220> FEATURE:
<223> OTHER INFORMATION: constructed sequence

<400> SEQUENCE: 7
aaggctcaga ggcacacagg agtttctggg ctcaccctgc cccctttccaa cccctcagtt        60 cccatcctcc agcagctgtt tgtgtgctgc ctctgaagtc cacactgaac aaacttcagc        120
ctactcatgt ccctaaaatg ggcaaacatt gcaagcagca aacagcaaac acacagccct        180
ccctgcctgc tgaccttgga gctggggcag aggtcagaga cctctctggg cccatgccac        240
ctccaacatc cactcgaccc cttggaattt cggtggagag gagcagaggt tgtcctggcg        300
tggtttaggt agtgtgagag gg                                                 322

<210> SEQ ID NO 8
<211> LENGTH: 176
<212> TYPE: DNA
<213> ORGANISM: Artificial Sequence
<220> FEATURE:
<223> OTHER INFORMATION: constructed sequence

<400> SEQUENCE: 8
actcaaagtt caaaccttat cattttttgc tttgttcctc ttggccttgg ttttgtacat        60
cagctttgaa aataccatcc cagggttaat gctggggtta atttataact aagagtgctc        120
tagttttgca atacaggaca tgctataaaa atggaaagat gttgctttct gagaga           176

<210> SEQ ID NO 9
<211> LENGTH: 477
<212> TYPE: DNA
<213> ORGANISM: Artificial Sequence
<220> FEATURE:
<223> OTHER INFORMATION: constructed sequence

<400> SEQUENCE: 9
agggctggaa gctacctttg acatcatttc ctctgcgaat gcatgtataa tttctacaga        60
acctattaga aaggatcacc cagcctctgc ttttgtacaa ctttcccttta aaaaactgcc       120 aattccactg ctgtttggcc caatagtgag aactttttcc tgctgcctct tggtgctttt        180
gcctatggcc cctattctgc ctgctgaaga cactcttgcc agcatggact taaacccctc        240
cagctctgac aatcctcttt ctcttttgtt ttacatgaag ggtctggcag ccaaagcaat        300
cactcaaagt tcaaacctta tcattttttg ctttgttcct cttggccttg gttttgtaca        360
tcagctttga aaataccatc ccagggttaa tgctggggtt aatttataac taagagtgct        420
ctagttttgc aatacaggac atgctataaa aatggaaaga tgttgctttc tgagaga          477

<210> SEQ ID NO 10
```

```
<211> LENGTH: 218
<212> TYPE: DNA
<213> ORGANISM: Artificial Sequence
<220> FEATURE:
<223> OTHER INFORMATION: constructed sequence

<400> SEQUENCE: 10
tggacacagg acgctgtggt ttctgagcca gggggcgact cagatcccag ccagtggact      60
tagcccctgt ttgctcctcc gataactggg gtgaccttgg ttaatattca ccagcagcct     120
cccccgttgc ccctctggat ccactgctta aatacggacg aggacagggc cctgtctcct     180
cagcttcagg caccaccact gacctgggac agtgaata                            218

<210> SEQ ID NO 11
<211> LENGTH: 190
<212> TYPE: DNA
<213> ORGANISM: Artificial Sequence
<220> FEATURE:
<223> OTHER INFORMATION: constructed sequence

<400> SEQUENCE: 11
atttcataga acgaatgttc cgatgctcta atctctctag acaaggttca tatttgtatg      60
ggttacttat tctctctttg ttgactaagt caataatcag aatcagcagg tttgcagtca     120
gattggcagg gataagcagc ctagctcagg agaagtgagt ataaaagccc caggctggga     180
gcagccatca                                                          190

<210> SEQ ID NO 12
<211> LENGTH: 215
<212> TYPE: DNA
<213> ORGANISM: Artificial Sequence
<220> FEATURE:
<223> OTHER INFORMATION: constructed sequence

<400> SEQUENCE: 12
gcctcgactg tgccttctag ttgccagcca tctgttgttt gccctcccc cgtgccttcc       60 ttgaccctgg aaggtgccac tcccactgtc ctttcctaat aaaatgagga aattgcatcg     120
cattgtctga gtaggtgtca ttctattctg gggggtgggg tggggcagga cagcaagggg     180
gaggattggg aagacaatag caggcatgct gggga                               215

<210> SEQ ID NO 13
<211> LENGTH: 572
<212> TYPE: DNA
<213> ORGANISM: Artificial Sequence
<220> FEATURE:
<223> OTHER INFORMATION: constructed sequence

<400> SEQUENCE: 13
agcttacttg tggtaccgag ctcggatcct gagaacttca gggtgagtct atgggaccct      60
tgatgttttc tttccccttc ttttctatgg ttaagttcat gtcataggaa ggggagaagt     120
aacagggtac acatattgac caaatcaggg taattttgca tttgtaattt taaaaaatgc     180
tttcttcttt taatatactt ttttgtttat cttatttcta atactttccc taatctcttt     240
ctttcagggc aataatgata caatgtatca tgcctctttg caccattcta aagaataaca     300
gtgataattt ctgggttaag gcaatagcaa tatttctgca tataaatatt tctgcatata     360
aattgtaact gatgtaagag gtttcatatt gctaatagca gctacaatcc agctaccatt     420
ctgcttttat tttatggttg ggataaggct ggattattct gagtccaagc taggcccttt     480
tgctaatcat gttcatacct cttatcttcc tcccacagct cctgggcaac gtgctggtct     540
```

-continued

```
gtgtgctggc ccatcacttt ggcaaagaat tg                                        572

<210> SEQ ID NO 14
<211> LENGTH: 1356
<212> TYPE: DNA
<213> ORGANISM: Artificial Sequence
<220> FEATURE:
<223> OTHER INFORMATION: constructed sequence

<400> SEQUENCE: 14
atgtctaccg ccgtgctgga aaatcccggc ctgggcagaa agctgagcga cttcggccag    60
gaaaccagct acatcgagga caactgcaac cagaacggcg ccatcagcct gatcttcagc   120
ctgaaagaag aagtgggcgc cctggccaag gtgctgcggc tgttcgaaga gaacgacgtg   180 aacctgacce acatcgagag ccggcccagc agactgaaga aggacgagta cgagttcttc   240
acccacctgg acaagcggag cctgcccgcc ctgaccaaca tcatcaagat cctgcggcac   300
gacatcggcg ccaccgtgca cgagctgagc cgggacaaga aaaaggacac cgtgccctgg   360
ttcccccgga ccatccagga actggacaga ttcgccaacc agatcctgag ctacggcgcc   420
gagctggacg ccgatcaccc cggctttaag acccccgtgt accgggccag acggaagcag   480
tttgccgata tcgcctacaa ctaccggcac ggccagccca tcccccgggt ggagtatatg   540
gaagaggaaa agaaaacctg gggcaccgtg ttcaagaccc tgaagtccct gtacaagacc   600
cacgcctgct acgagtacaa ccacatcttc ccactgctgg aaaagtactg cggcttccac   660
gaggacaata tcccccagct ggaagacgtg tcccagttcc tgcagacctg caccggcttc   720
agactgaggc ctgtggccgg actgctgagc agcagagatt ttctgggcgg actggccttc   780
cgggtgttcc actgcaccca gtacatcaga cacggcagca agcccatgta cacccccgag   840
cccgatatct gccacgagct gctgggacac gtgcccctgt tcagcgacag aagcttcgcc   900
cagttcagcc aggaaatcgg cctggcctct ctgggagccc ccgacgagta tatcgagaag   960
ctggccacca tctactggtt caccgtggaa ttcggcctgt gcaagcaggg cgacagcatc  1020
aaggcctacg gcgctggcct gctgtccagc tttggcgagc tgcagtactg tctgagcgag  1080
aagcccaagc tgctgcccct ggaactggaa aagaccgcca tccagaacta caccgtgacc  1140
gagttccagc ccctgtacta cgtggccgag agcttcaacg acgccaaaga aaaagtgcgg  1200
aacttcgccg ccaccatccc cagaccattc tccgtcagat acgacccta cacccagcgg  1260 atcgaggtgc tggacaacac acagcagctg aaaattctgg ccgactccat caacagcgag  1320
atcggcatcc tgtgcagcgc cctgcagaag atcaag                            1356

<210> SEQ ID NO 15
<211> LENGTH: 542
<212> TYPE: DNA
<213> ORGANISM: Artificial Sequence
<220> FEATURE:
<223> OTHER INFORMATION: constructed sequence

<400> SEQUENCE: 15
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact   240 ggttgggca ttgccaccac ctgtcagctc ctttccggga ctttcgcttt ccccctccct   300
```

-continued attgccacgg cggaactcat cgccgcctgc cttgcccgct gctggacagg ggctcggctg      360
ttgggcactg acaattccgt ggtgttgtcg gggaaatcat cgtcctttcc ttggctgctc      420
gcctgtgttg ccacctggat tctgcgcggg acgtccttct gctacgtccc ttcggccctc      480
aatccagcgg accttccttc ccgcggcctg ctgccggctc tgcggcctct tccgcgtctt      540
cg                                                                     542

<210> SEQ ID NO 16
<211> LENGTH: 168
<212> TYPE: DNA
<213> ORGANISM: Artificial Sequence
<220> FEATURE:
<223> OTHER INFORMATION: constructed sequence

<400> SEQUENCE: 16
ctgcgcgctc gctcgctcac tgaggccgcc cgggcaaagc ccgggcgtcg ggcgaccttt       60
ggtcgcccgg cctcagtgag cgagcgagcg cgcagagagg gagtggccaa ctccatcact      120
aggggttcct tgtagttaat gattaacccg ccatgctact tatctacg                  168

<210> SEQ ID NO 17
<211> LENGTH: 168
<212> TYPE: DNA
<213> ORGANISM: Artificial Sequence
<220> FEATURE:
<223> OTHER INFORMATION: constructed sequence

<400> SEQUENCE: 17
cgtagataag tagcatggcg ggttaatcat taactacaag gaacccctag tgatggagtt       60
ggccactccc tctctgcgcg ctcgctcgct cactgaggcc gggcgaccaa aggtcgcccg      120
acgcccgggc tttgcccggg cggcctcagt gagcgagcga gcgcgcag                  168

<210> SEQ ID NO 18
<211> LENGTH: 1421
<212> TYPE: DNA
<213> ORGANISM: Artificial Sequence
<220> FEATURE:
<223> OTHER INFORMATION: constructed sequence

<400> SEQUENCE: 18
gtttgtttcc tttttaaaa tacattgagt atgcttgcct tttagatata gaaatatctg       60
atgctgtctt cttcactaaa ttttgattac atgatttgac agcaatattg aagagtctaa      120
cagccagcac gcaggttggt aagtactggt tctttgttag ctaggttttc ttcttcttca      180
tttttaaaac taaatagatc gacaatgctt atgatgcatt tatgtttaat aaacactgtt      240
cagttcatga tttggtcatg taattcctgt tagaaaacat tcatctcctt ggtttaaaaa      300
aattaaaagt gggaaaacaa agaaatagca gaatatagtg aaaaaaaata accacattat      360
ttttgtttgg acttaccact ttgaaatcaa aatgggaaac aaaagcacaa acaatggcct      420
tatttacaca aaaagtctga ttttaagata tatgacattt caaggtttca gaagtatgta      480
atgaggtgtg tctctaattt tttaaattat atatcttcaa tttaaagttt tagttaaaac      540
ataaagatta acctttcatt agcaagctgt tagttatcac caaagctttt catggattag      600
gaaaaaatca ttttgtctct atgtcaaaca tcttggagtt gatatttggg gaaacacaat      660
actcagttga gttccctagg ggagaaaagc aagcttaaga attgacataa agagtaggaa      720
gttagctaat gcaacatata tcactttgtt ttttcacaac tacagtgact ttatgtattt      780
cccagaggaa ggcatacagg gaagaaatta tcccatttgg acaaacagca tgttctcaca      840

-continued

```
ggaagcattt atcacactta cttgtcaact ttctagaatc aaatctagta gctgacagta      900
ccaggatcag gggtgccaac cctaagcacc cccagaaagc tgactggccc tgtggttccc      960
actccagaca tgatgtcagc tggaccataa ttaggcttct gttcttcagg agacatttgt     1020
tcaaagtcat ttgggcaacc atattctgaa aacagcccag ccagggtgat ggatcacttt     1080
gcaaagatcc tcaatgagct attttcaagt gatgacaaag tgtgaagtta accgctcatt     1140
tgagaacttt cttttccatc caaagtaaat tcaaatatga ttagaaatct gaccttttat     1200
tactggaatt ctcttgacta aaagtaaaat tgaattttaa ttcctaaatc tccatgtgta     1260
tacagtactg tgggaacatc acagattttg gctccatgcc ctaaagagaa attggctttc     1320
agattatttg gattaaaaac aaagactttc ttaagagatg taaaattttc atgatgtttt     1380
cttttttgct aaaactaaag aattattctt ttacatttca g                        1421
```

<210> SEQ ID NO 19
<211> LENGTH: 738
<212> TYPE: PRT
<213> ORGANISM: Unknown
<220> FEATURE:
<223> OTHER INFORMATION: AAV8

<400> SEQUENCE: 19

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255
```

-continued

```
Leu Tyr Lys Gln Ile Ser Asn Gly Thr Ser Gly Gly Ala Thr Asn Asp
        260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
        450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
                580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
        660                 665                 670

Ile Thr Gln Tyr Ser Thr Gly Gln Val Ser Val Glu Ile Glu Trp Glu
```

```
            675              680              685
Leu Gln Lys Glu Asn Ser Lys Arg Trp Asn Pro Glu Ile Gln Tyr Thr
    690              695              700

Ser Asn Tyr Tyr Lys Ser Thr Ser Val Asp Phe Ala Val Asn Thr Glu
705              710              715              720

Gly Val Tyr Ser Glu Pro Arg Pro Ile Gly Thr Arg Tyr Leu Thr Arg
                725              730              735

Asn Leu

<210> SEQ ID NO 20
<211> LENGTH: 3445
<212> TYPE: DNA
<213> ORGANISM: Artificial Sequence
<220> FEATURE:
<223> OTHER INFORMATION: constructed sequence

<400> SEQUENCE: 20
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gccatgctct     180
aggaagatcg gaattcgccc ttaagctagc aggttaattt ttaaaaagca gtcaaaagtc     240
caagtggccc ttggcagcat ttactctctc tgtttgctct ggttaataat ctcaggagca     300
caaacattcc agatccaggt taattttaa aaagcagtca aaagtccaag tggcccttgg     360
cagcatttac tctctctgtt tgctctggtt aataatctca ggagcacaaa cattccagat     420
ccggcgcgcc agggctggaa gctacctttg acatcatttc ctctgcgaat gcatgtataa     480
tttctacaga acctattaga aaggatcacc cagcctctgc ttttgtacaa ctttcccta     540 aaaaactgcc aattccactg ctgtttggcc caatagtgag aactttttcc tgctgcctct     600
tggtgctttt gccatggcc cctattctgc ctgctgaaga cactcttgcc agcatggact     660
taaacccctc cagctctgac aatcctcttt ctcttttgtt ttacatgaag ggtctggcag     720
ccaaagcaat cactcaaagt tcaaacctta tcatttttg ctttgttcct cttggccttg     780
gttttgtaca tcagctttga aaataccatc ccagggttaa tgctgggt aatttataac     840 taagagtgct ctagttttgc aatacaggac atgctataaa aatggaaaga tgttgctttc     900
tgagagactg cagaagttgg tcgtgaggca ctgggcaggt aagtatcaag gttacaagac     960
aggtttaagg agaccaatag aaactgggct tgtcgagaca gagaagactc ttgcgtttct    1020
gataggcacc tattggtctt actgacatcc actttgcctt tctctccaca ggtgtccagg    1080
cggccgccac catgtctacc gccgtgctgg aaaatcccgg cctgggcaga aagctgagcg    1140
acttcggcca ggaaaccagc tacatcgagg acaactgcaa ccagaacggc gccatcagcc    1200
tgatcttcag cctgaaagaa gaagtgggcg ccctggccaa ggtgctgcgg ctgttcgaag    1260
agaacgacgt gaacctgacc cacatcgaga gccggcccag cagactgaag aaggacagt    1320 acgagttctt cacccacctg gacaagcgga gcctgccgc cctgaccaac atcatcaaga    1380
tcctgcggca cgacatcggc gccaccgtgc acgagctgag ccgggacaag aaaaaggaca    1440
ccgtgccctg gttcccccgg accatccagg aactggacag attcgccaac cagatcctga    1500
gctacggcgc cgagctggac gccgatcacc ccggctttaa ggaccccgtg taccgggcca    1560
gacggaagca gtttgccgat atcgcctaca ctaccggca cggccagccc atcccccggg    1620
tggagtatat ggaagaggaa aagaaaacct ggggcaccgt gttcaagacc ctgaagtccc    1680
```

-continued

```
tgtacaagac ccacgcctgc tacgagtaca accacatctt cccactgctg gaaaagtact      1740
gcggcttcca cgaggacaat atccccagc tggaagacgt gtcccagttc ctgcagacct       1800
gcaccggctt cagactgagg cctgtggccg gactgctgag cagcagagat tttctgggcg      1860
gactggcctt ccgggtgttc cactgcaccc agtacatcag acacggcagc aagcccatgt      1920 acaccccga gcccgatatc tgccacgagc tgctgggaca cgtgcccctg ttcagcgaca       1980
gaagcttcgc ccagttcagc caggaaatcg gcctggcctc tctgggagcc cccgacgagt      2040
atatcgagaa gctggccacc atctactggt tcaccgtgga attcggcctg tgcaagcagg      2100
gcgacagcat caaggcctac ggcgctggcc tgctgtccag ctttggcgag ctgcagtact      2160
gtctgagcga gaagcccaag ctgctgcccc tggaactgga aaagaccgcc atccagaact      2220
acaccgtgac cgagttccag cccctgtact acgtggccga gagcttcaac gacgccaaag      2280
aaaaagtgcg gaacttcgcc gccaccatcc ccagaccatt ctccgtcaga tacgacccct      2340
acacccagcg gatcgaggtg ctggacaaca cacagcagct gaaaattctg gccgactcca      2400
tcaacagcga gatcggcatc ctgtgcagcg ccctgcagaa gatcaagtga taagcatgcg      2460
gatccaatca acctctggat tacaaaattt gtgaaagatt gactggtatt cttaactatg      2520
ttgctccttt tacgctatgt ggatacgctg ctttaatgcc tttgtatcat gctattgctt      2580
cccgtatggc tttcatttc tcctccttgt ataaatcctg gttgctgtct ctttatgagg      2640
agttgtggcc cgttgtcagg caacgtggcg tggtgtgcac tgtgtttgct gacgcaaccc      2700
ccactggttg gggcattgcc accacctgtc agctcctttc cgggactttc gctttcccc      2760 tccctattgc cacggcggaa ctcatcgccg cctgccttgc ccgctgctgg acaggggctc      2820
ggctgttggg cactgacaat tccgtggtgt tgtcggggaa atcatcgtcc tttccttggc      2880
tgctcgcctg tgttgccacc tggattctgc gcgggacgtc cttctgctac gtcccttcgg      2940
ccctcaatcc agcggacctt ccttcccgcg gcctgctgcc ggctctgcgg cctcttccgc      3000
gtcttcgaga tctgcctcga ctgtgccttc tagttgccag ccatctgttg tttgccctc       3060 ccccgtgcct tccttgaccc tggaaggtgc cactcccact gtcctttcct aataaaatga     3120
ggaaattgca tcgcattgtc tgagtaggtg tcattctatt ctggggggtg gggtggggca      3180
ggacagcaag ggggaggatt gggaagacaa tagcaggcat gctggggact cgagttaagg      3240
gcgaattccc gataaggatc ttcctagagc atggctacgt agataagtag catggcgggt      3300
taatcattaa ctacaaggaa cccctagtga tggagttggc cactccctct ctgcgcgctc      3360
gctcgctcac tgaggccggg cgaccaaagg tcgcccgacg cccgggcttt gcccgggcgg      3420
cctcagtgag cgagcgagcg cgcag                                          3445
```

<210> SEQ ID NO 21
<211> LENGTH: 2897
<212> TYPE: DNA
<213> ORGANISM: Artificial Sequence
<220> FEATURE:
<223> OTHER INFORMATION: constructed sequence

<400> SEQUENCE: 21

```
ctgcgcgctc gctcgctcac tgaggccgcc cgggcaaagc ccgggcgtcg ggcgaccttt        60
ggtcgcccgg cctcagtgag cgagcgagcg cgcagagagg gagtggccaa ctccatcact       120
aggggttcct tgtagttaat gattaacccg ccatgctact tatctacgta gccatgctct       180
aggaagatcg gaattcgccc ttaagctagc aggttaattt ttaaaaagca gtcaaaagtc       240
caagtggccc ttggcagcat ttactctctc tgtttgctct ggttaataat ctcaggagca       300
```

-continued

```
caaacattcc agatccaggt taatttttaa aaagcagtca aaagtccaag tggcccttgg      360
cagcatttac tctctctgtt tgctctggtt aataatctca ggagcacaaa cattccagat      420
ccggcgcgcc agggctggaa gctacctttg acatcatttc ctctgcgaat gcatgtataa      480
tttctacaga acctattaga aaggatcacc cagcctctgc ttttgtacaa ctttcccta      540 aaaaactgcc aattccactg ctgtttggcc caatagtgag aacttttttcc tgctgcctct      600 tggtgctttt gcctatggcc cctattctgc ctgctgaaga cactcttgcc agcatggact      660
taaacccctc cagctctgac aatcctcttt ctcttttgtt ttacatgaag ggtctggcag      720
ccaaagcaat cactcaaagt tcaaacctta tcattttttg ctttgttcct cttggccttg      780
gttttgtaca tcagctttga aaataccatc ccagggttaa tgctggggtt aatttataac      840
taagagtgct ctagttttgc aatacaggac atgctataaa aatggaaaga tgttgctttc      900
tgagagactg cagaagttgg tcgtgaggca ctgggcaggt aagtatcaag gttacaagac      960
aggtttaagg agaccaatag aaactgggct tgtcgagaca gagaagactc ttgcgtttct     1020
gataggcacc tattggtctt actgacatcc actttgcctt tctctccaca ggtgtccagg     1080
cggccgccac catgtctacc gccgtgctgg aaaatcccgg cctgggcaga aagctgagcg     1140
acttcggcca ggaaaccagc tacatcgagg acaactgcaa ccagaacggc gccatcagcc     1200
tgatcttcag cctgaaagaa gaagtgggcg ccctggccaa ggtgctgcgg ctgttcgaag     1260
agaacgacgt gaacctgacc cacatcgaga gccggcccag cagactgaag aaggacgagt     1320
acgagttctt cacccacctg gacaagcgga gcctgcccgc cctgaccaac atcatcaaga     1380
tcctgcggca cgacatcggc gccaccgtgc acagctgag ccgggacaag aaaaaggaca     1440
ccgtgccctg gttcccccgg accatccagg aactggacag attcgccaac cagatcctga     1500
gctacggcgc cgagctggac gccgatcacc ccggctttaa ggaccccgtg taccgggcca     1560
gacggaagca gtttgccgat atcgcctaca actaccggca cggccagccc atcccccggg     1620
tggagtatat ggaagaggaa aagaaaacct ggggcaccgt gttcaagacc ctgaagtccc     1680
tgtacaagac ccacgcctgc tacgagtaca accacatctt cccactgctg gaaaagtact     1740
gcggcttcca cgaggacaat atccccagc tggaagacgt gtcccagttc ctgcagacct     1800
gcaccggctt cagactgagg cctgtggccg gactgctgag cagcagagat tttctgggcg     1860
gactggcctt ccgggtgttc cactgcaccc agtacatcag acacggcagc aagcccatgt     1920
acacccccga gcccgatatc tgccacgagc tgctgggaca cgtgcccctg ttcagcgaca     1980
gaagcttcgc ccagttcagc caggaaatcg gcctggcctc tctgggagcc cccgacgagt     2040
atatcgagaa gctggccacc atctactggt tcaccgtgga attcggcctg tgcaagcagg     2100
gcgacagcat caaggcctac ggcgctggcc tgctgtccag cttttggcgag ctgcagtact     2160 gtctgagcga gaagcccaag ctgctgcccc tggaactgga aaagaccgcc atccagaact     2220
acaccgtgac cgagttccag cccctgtact acgtggccga gagcttcaac gacgccaaag     2280
aaaaagtgcg gaacttcgcc gccaccatcc ccagaccatt ctccgtcaga tacgacccct     2340
acacccagcg gatcgaggtg ctggacaaca cacagcagct gaaaattctg gccgactcca     2400
tcaacagcga gatcggcatc ctgtgcagcg ccctgcagaa gatcaagtga taagcatgcg     2460
gatctgcctc gactgtgcct tctagttgcc agccatctgt tgtttgcccc tcccccgtgc     2520
cttccttgac cctggaaggt gccactccca ctgtcctttc ctaataaaat gaggaaattg     2580
catcgcattg tctgagtagg tgtcattcta ttctggggggg tggggtgggg caggacagca     2640
```

```
aggggggagga ttgggaagac aatagcaggc atgctgggga ctcgagttaa gggcgaattc     2700
ccgataagga tcttcctaga gcatggctac gtagataagt agcatggcgg gttaatcatt     2760
aactacaagg aaccctagt gatggagttg gccactccct ctctgcgcgc tcgctcgctc      2820
actgaggccg ggcgaccaaa ggtcgcccga cgcccgggct ttgcccgggc ggcctcagtg     2880
agcgagcgag cgcgcag                                                    2897

<210> SEQ ID NO 22
<211> LENGTH: 3341
<212> TYPE: DNA
<213> ORGANISM: Artificial Sequence
<220> FEATURE:
<223> OTHER INFORMATION: constructed sequence

<400> SEQUENCE: 22
ctgcgcgctc gctcgctcac tgaggccgcc cgggcaaagc ccgggcgtcg ggcgaccttt       60
ggtcgcccgg cctcagtgag cgagcgagcg cgcagagagg gagtggccaa ctccatcact      120
aggggttcct tgtagttaat gattaacccg ccatgctact tatctacgta gccatgctct      180
aggaagatcg gaattcgccc ttaagctagg agttaatttt taaaaagcag tcaaaagtcc      240
aagtgccctt gcgagcattt actctctctg tttgctctgg ttaataatct caggagcaca      300
aacattcctt actagttcta ggagttaatt tttaaaaagc agtcaaaagt ccaagtgccc      360
ttgcgagcat ttactctctc tgtttgctct ggttaataat ctcaggagca caaacattcc      420
ttactagttc tagagcggcc gccagtgtgc tggaattcgg ctttttttagg gctggaagct      480 acctttgaca tcatttcctc tgcgaatgca tgtataattt ctacagaacc tattagaaag      540
gatcacccag cctctgcttt tgtacaactt cccttaaaa aactgccaat cccactgctg       600
tttggcccaa tagtgagaac ttttttcctgc tgcctcttgg tgcttttgcc tatggcccct      660
attctgcctg ctgaagacac tcttgccagc atggacttaa acccctccag ctctgacaat      720
cctctttctc ttttgtttta catgaagggt ctggcagcca aagcaatcac tcaaagttca      780
aaccttatca tttttttgctt tgttcctctt ggccttggtt ttgtacatca gctttgaaaa      840
taccatccca gggttaatgc tggggttaat ttataactga gagtgctcta gttctgcaat      900
acaggacatg ctataaaaat ggaaagatgt tgctttctga gagatcagct tacttgtggt      960
accgagctcg gatcctgaga acttcagggt gagtctatgg gacccttgat gttttctttc     1020
cccttctttt ctatggttaa gttcatgtca taggaagggg agaagtaaca gggtacacat     1080
attgaccaaa tcagggtaat tttgcatttg taattttaaa aaatgctttc ttcttttaat     1140
atactttttt gtttatctta tttctaatac tttccctaat ctctttcttt cagggcaata     1200
atgatacaat gtatcatgcc tctttgcacc attctaaaga ataacagtga taatttctgg     1260
gttaaggcaa tagcaatatt tctgcatata aatatttctg catataaatt gtaactgatg     1320
taagaggttt catattgcta atagcagcta caatccagct accattctgc ttttattta      1380 tggttgggat aaggctggat tattctgagt ccaagctagg cccttttgct aatcatgttc     1440
atacctctta tcttcctccc acagctcctg ggcaacgtgc tggtctgtgt gctggcccat     1500
cactttggca agaattgat ctcgaggccg ccaccatgtc taccgccgtg ctggaaaatc      1560
ccggcctggg cagaaagctg agcgacttcg gccaggaaac cagctacatc gaggacaact     1620
gcaaccagaa cggcgccatc agcctgatct tcagcctgaa agaagaagtg ggcgccctgg     1680
ccaaggtgct gcggctgttc gaagagaacg acgtgaacct gacccacatc gagagccggc     1740
ccagcagact gaagaaggac gagtacgagt tcttcaccca cctggacaag cggagcctgc     1800
```
ccgccctgac caacatcatc aagatcctgc ggcacgacat cggcgccacc gtgcacgagc      1860
tgagccggga caagaaaaag gacaccgtgc cctggttccc ccggaccatc caggaactgg      1920
acagattcgc caaccagatc ctgagctacg gcgccgagct ggacgccgat cacccccggct      1980 ttaaggaccc cgtgtaccgg gccagacgga agcagtttgc cgatatcgcc tacaactacc      2040
ggcacggcca gcccatcccc cgggtggagt atatggaaga ggaaaagaaa acctggggca      2100
ccgtgttcaa gaccctgaag tccctgtaca gacccacgc ctgctacgag tacaaccaca      2160
tcttcccact gctggaaaag tactgcggct ccacgagga caatatcccc cagctggaag      2220
acgtgtccca gttcctgcag acctgcaccg gcttcagact gaggcctgtg gccggactgc      2280
tgagcagcag agattttctg ggcggactgg ccttccgggt gttccactgc acccagtaca      2340
tcagacacgg cagcaagccc atgtacaccc ccgagcccga tatctgccac gagctgctgg      2400
gacacgtgcc cctgttcagc gacagaagct cgcccagtt cagccaggaa atcggcctgg      2460
cctctctggg agcccccgac gagtatatcg agaagctggc caccatctac tggttcaccg      2520
tggaattcgg cctgtgcaag cagggcgaca gcatcaaggc ctacggcgct ggcctgctgt      2580
ccagctttgg cgagctgcag tactgtctga gcgagaagcc caagctgctg ccctggaac      2640 tggaaaagac cgccatccag aactacaccg tgaccgagtt ccagcccctg tactacgtgg      2700
ccgagagctt caacgacgcc aaagaaaaag tgcggaactt cgccgccacc atccccagac      2760
cattctccgt cagatacgac ccctacaccc agcggatcga ggtgctggac aacacacagc      2820
agctgaaaat tctggccgac tccatcaaca gcgagatcgg catcctgtgc agcgccctgc      2880
agaagatcaa gtgataagca tgcggatctg cctcgactgt gccttctagt tgccagccat      2940
ctgttgtttg cccctccccc gtgccttcct tgaccctgga aggtgccact cccactgtcc      3000
tttcctaata aaatgaggaa attgcatcgc attgtctgag taggtgtcat tctattctgg      3060
ggggtggggt ggggcaggac agcaaggggg aggattggga agacaatagc aggcatgctg      3120
gggactcgag ttaagggcga attcccgata aggatcttcc tagagcatgg ctacgtagat      3180
aagtagcatg gcgggttaat cattaactac aaggaacccc tagtgatgga gttggccact      3240
ccctctctgc gcgctcgctc gctcactgag gccgggcgac caaaggtcgc ccgacgcccg      3300
ggctttgccc gggcggcctc agtgagcgag cgagcgcgca g                         3341

<210> SEQ ID NO 23
<211> LENGTH: 2203
<212> TYPE: DNA
<213> ORGANISM: Artificial Sequence
<220> FEATURE:
<223> OTHER INFORMATION: constructed sequence

<400> SEQUENCE: 23
ctgcgcgctc gctcgctcac tgaggccgcc cgggcaaagc ccgggcgtcg ggcgaccttt        60
ggtcgcccgg cctcagtgag cgagcgagcg cgcagagagg gagtggccaa ctccatcact       120
aggggttcct tgtagttaat gattaacccg ccatgctact tatctactta agtgtttgct       180
gcttgcaatg tttgcccatt ttaggggaat tctggacaca ggacgctgtg gtttctgagc       240
cagggggcga ctcagatccc agccagtgga cttagcccct gtttgctcct ccgataactg       300
gggtgacctt ggttaatatt caccagcagc ctcccccgtt gcccctctgg atccactgct       360
taaatacgga cgaggacagg gccctgtctc ctcagcttca ggcaccacca ctgacctggg       420
acagtgaata gcggccgcca ccatgtctac cgccgtgctg gaaaatcccg gcctgggcag       480

-continued

```
aaagctgagc gacttcggcc aggaaaccag ctacatcgag gacaactgca accagaacgg      540
cgccatcagc ctgatcttca gcctgaaaga agaagtgggc gccctggcca aggtgctgcg      600
gctgttcgaa gagaacgacg tgaacctgac ccacatcgag agccggccca gcagactgaa      660
gaaggacgag tacgagttct tcacccacct ggacaagcgg agcctgcccg ccctgaccaa      720
catcatcaag atcctgcggc acgacatcgg cgccaccgtg cacgagctga gccgggacaa      780
gaaaaaggac accgtgccct ggttcccccg gaccatccag gaactggaca gattcgccaa      840
ccagatcctg agctacggcg ccgagctgga cgccgatcac cccggcttta aggaccccgt      900
gtaccgggcc agacggaagc agtttgccga tatcgcctac aactaccggc acggccagcc      960
catcccccgg gtggagtata tggaagagga aaagaaaacc tggggcaccg tgttcaagac     1020
cctgaagtcc ctgtacaaga cccacgcctg ctacgagtac aaccacatct cccactgct     1080 ggaaaagtac tgcggcttcc acgaggacaa tatcccccag ctggaagacg tgtcccagtt     1140
cctgcagacc tgcaccggct tcagactgag gcctgtggcc ggactgctga gcagcagaga     1200
ttttctgggc ggactggcct ccgggtgtt ccactgcacc cagtacatca gacacggcag     1260
caagcccatg tacacccccg agcccgatat ctgccacgag ctgctgggac acgtgcccct     1320
gttcagcgac agaagcttcg cccagttcag ccaggaaatc ggcctggcct ctctgggagc     1380 cccccgacgag tatatcgaga agctggccac catctactgg ttcaccgtgg aattcggcct     1440
gtgcaagcag ggcgacagca tcaaggccta cggcgctggc ctgctgtcca gctttggcga     1500
gctgcagtac tgtctgagcg agaagcccaa gctgctgccc ctggaactgg aaaagaccgc     1560
catccagaac tacaccgtga ccgagttcca gcccctgtac tacgtggccg agagcttcaa     1620
cgacgccaaa gaaaaagtgc ggaacttcgc cgccaccatc cccagaccat tctccgtcag     1680
atacgacccc tacacccagc ggatcgaggt gctggacaac acacagcagc tgaaaattct     1740
ggccgactcc atcaacagcg agatcggcat cctgtgcagc gccctgcaga agatcaagtg     1800
ataagcatgc ggatctgcct cgactgtgcc ttctagttgc cagccatctg ttgtttgccc     1860
ctcccccgtg ccttccttga ccctggaagg tgccactccc actgtccttt cctaataaaa     1920
tgaggaaatt gcatcgcatt gtctgagtag gtgtcattct attctggggg gtggggtggg     1980
gcaggacagc aagggggagg attgggaaga caatagcagg catgctgggg actcgagtag     2040
ataagtagca tggcgggtta atcattaact acaggaacc cctagtgatg gagttggcca      2100
ctccctctct gcgcgctcgc tcgctcactg aggccgggcg accaaaggtc gcccgacgcc     2160
cgggctttgc ccgggcggcc tcagtgagcg agcgagcgcg cag                       2203
```

<210> SEQ ID NO 24
<211> LENGTH: 2496
<212> TYPE: DNA
<213> ORGANISM: Artificial Sequence
<220> FEATURE:
<223> OTHER INFORMATION: constructed sequence

<400> SEQUENCE: 24

```
ctgcgcgctc gctcgctcac tgaggccgcc cgggcaaagc ccgggcgtcg ggcgaccttt       60
ggtcgcccgg cctcagtgag cgagcgagcg cgcagagagg gagtggccaa ctccatcact      120
aggggttcct tgtagttaat gattaacccg ccatgctact tatctacgta gccatgctct      180
aggaagatcg gaattcgccc ttaagctagc ctacctcgtg atcgcccggc ccctgttcaa      240
acatgtccta atactctgtc tctgcaaggg tcatcagtag ttttccatct tactcaacat      300
cctcccagtg gaattcattt catagaacga atgttccgat gctctaatct ctctagacaa      360
```

```
ggttcatatt tgtatgggtt acttattctc tctttgttga ctaagtcaat aatcagaatc        420
agcaggtttg cagtcagatt ggcagggata agcagcctag ctcaggagaa gtgagtataa        480
aagccccagg ctgggagcag ccatcactgc agaagttggt cgtgaggcac tgggcaggta        540
agtatcaagg ttacaagaca ggtttaagga gaccaataga aactgggctt gtcgagacag        600
agaagactct tgcgtttctg ataggcacct attggtctta ctgacatcca ctttgccttt        660
ctctccacag gtgtccaggc ggccgccacc atgtctaccg ccgtgctgga aaatcccggc        720
ctgggcagaa agctgagcga cttcggccag gaaaccagct acatcgagga caactgcaac        780
cagaacggcg ccatcagcct gatcttcagc ctgaaagaag aagtgggcgc cctggccaag        840
gtgctgcggc tgttcgaaga gaacgacgtg aacctgaccc acatcgagag ccggcccagc        900
agactgaaga aggacgagta cgagttcttc acccacctgg acaagcggag cctgcccgcc        960
ctgaccaaca tcatcaagat cctgcggcac gacatcggcg ccaccgtgca cgagctgagc       1020
cgggacaaga aaaaggacac cgtgccctgg ttccccggca ccatccagga actggacaga       1080
ttcgccaacc agatcctgag ctacggcgcc gagctggacg ccgatcaccc cggctttaag       1140
gaccccgtgt accgggccag acggaagcag tttgccgata tcgcctacaa ctaccggcac       1200
ggccagccca tcccccgggt ggagtatatg gaagaggaaa agaaaacctg gggcaccgtg       1260
ttcaagaccc tgaagtccct gtacaagacc cacgcctgct acgagtacaa ccacatcttc       1320
ccactgctgg aaaagtactg cggcttccac gaggacaata tcccccagct ggaagacgtg       1380
tcccagttcc tgcagacctg caccggcttc agactgaggc ctgtggccgg actgctgagc       1440
agcagagatt ttctgggcgg actggccttc cgggtgttcc actgcaccca gtacatcaga       1500
cacggcagca gcccatgta cacccccgag cccgatatct gccacgagct gctgggacac       1560
gtgcccctgt tcagcgacag aagcttcgcc cagttcagcc aggaaatcgg cctggcctct       1620
ctgggagccc ccgacgagta tatcgagaag ctggccacca tctactggtt caccgtggaa       1680
ttcggcctgt gcaagcaggg cgacagcatc aaggcctacg gcgctggcct gctgtccagc       1740
tttggcgagc tgcagtactg tctgagcgag aagcccaagc tgctgcccct ggaactggaa       1800
aagaccgcca tccagaacta caccgtgacc gagttccagc ccctgtacta cgtggccgag       1860
agcttcaacg acgccaaaga aaaagtgcgg aacttcgccg ccaccatccc cagaccattc       1920
tccgtcagat acgaccccta cacccagcgg atcgaggtgc tggacaacac acagcagctg       1980
aaaattctgg ccgactccat caacagcgag atcggcatcc tgtgcagcgc cctgcagaag       2040
atcaagtgat aagcatgcgg atctgcctcg actgtgcctt ctagttgcca gccatctgtt       2100
gtttgcccct cccccgtgcc ttccttgacc ctggaaggtg ccactcccac tgtcctttcc       2160
taataaaatg aggaaattgc atcgcattgt ctgagtaggt gtcattctat tctggggggt       2220
ggggtggggc aggacagcaa gggggaggat tgggaagaca atagcaggca tgctggggac       2280
tcgagttaag ggcgaattcc cgattaggat cttcctagag catggctacg tagataagta       2340
gcatggcggg ttaatcatta actacaagga accctagtg atggagttgg ccactccctc       2400
tctgcgcgct cgctcgctca ctgaggccgg gcgaccaaag gtcgcccgac gcccgggctt       2460
tgcccgggcg gcctcagtga gcgagcgagc gcgcag                                2496
```

<210> SEQ ID NO 25
<211> LENGTH: 2241
<212> TYPE: DNA
<213> ORGANISM: Artificial Sequence
<220> FEATURE:

<223> OTHER INFORMATION: constructed sequence

<400> SEQUENCE: 25

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctactta agctacctcg     180
tgatcgcccg gccctgttc aaacatgtcc taatactctg tctctgcaag ggtcatcagt     240
agttttccat cttactcaac atcctcccag tggaattcat ttcatagaac gaatgttccg     300
atgctctaat ctctctagac aaggttcata tttgtatggg ttacttattc tctctttgtt     360
gactaagtca ataatcagaa tcagcaggtt tgcagtcaga ttggcaggga taagcagcct     420
agctcaggag aagtgagtat aaaagcccca ggctgggagc agccatcagc ggccgccacc     480
atgtctaccg ccgtgctgga aaatcccggc ctgggcagaa agctgagcga cttcggccag     540
gaaaccagct acatcgagga caactgcaac cagaacggcg ccatcagcct gatcttcagc     600
ctgaaagaag aagtgggcgc cctggccaag gtgctgcggc tgttcgaaga gaacgacgtg     660
aacctgaccc acatcgagag ccggcccagc agactgaaga aggacgagta cgagttcttc     720
acccacctgg acaagcggag cctgcccgcc ctgaccaaca tcatcaagat cctgcggcac     780
gacatcggcg ccaccgtgca cgagctgagc cgggacaaga aaaaggacac cgtgccctgg     840
ttcccccgga ccatccagga actggacaga ttcgccaacc agatcctgag ctacggcgcc     900
gagctggacg ccgatcaccc cggctttaag dacccgtgt accgggccag acggaagcag     960
tttgccgata tcgcctacaa ctaccggcac ggccagccca tcccccgggt ggagtatatg    1020
gaagaggaaa agaaaacctg gggcaccgtg ttcaagaccc tgaagtccct gtacaagacc    1080
cacgcctgct acgagtacaa ccacatcttc ccactgctgg aaaagtactg cggcttccac    1140
gaggacaata tcccccagct ggaagacgtg tcccagttcc tgcagacctg caccggcttc    1200
agactgaggc ctgtggccgg actgctgagc agcagagatt ttctgggcgg actggccttc    1260
cgggtgttcc actgcaccca gtacatcaga cacggcagca gcccatgta caccccgag    1320 cccgatatct gccacgagct gctgggacac gtgcccctgt tcagcgacag aagcttcgcc    1380
cagttcagcc aggaaatcgg cctggcctct ctgggagccc ccgacgagta tatcgagaag    1440
ctggccacca tctactggtt caccgtggaa ttcggcctgt gcaagcaggg cgacagcatc    1500
aaggcctacg gcgctggcct gctgtccagc tttggcgagc tgcagtactg tctgagcgag    1560
aagcccaagc tgctgcccct ggaactggaa aagaccgcca tccagaacta caccgtgacc    1620
gagttccagc ccctgtacta cgtggccgag agcttcaacg acgccaaaga aaaagtgcgg    1680
aacttcgccg ccaccatccc cagaccattc tccgtcagat acgacccta cacccagcgg    1740 atcgaggtgc tggacaacac acagcagctg aaaattctgg ccgactccat caacagcgag    1800
atcggcatcc tgtgcagcgc cctgcagaag atcaagtgat aagcatgcgg atctgcctcg    1860
actgtgcctt ctagttgcca gccatctgtt gtttgcccct cccccgtgcc ttccttgacc    1920
ctggaaggtg ccactcccac tgtcctttcc taataaaatg aggaaattgc atcgcattgt    1980
ctgagtaggt gtcattctat tctggggggt ggggtggggc aggacagcaa ggggaggat    2040 tgggaagaca atagcaggca tgctggggac tcgagtagat aagtagcatg gcgggttaat    2100
cattaactac aaggaacccc tagtgatgga gttggccact ccctctctgc gcgctcgctc    2160
gctcactgag gccgggcgac caaaggtcgc ccgacgcccg ggctttgccc gggcggcctc    2220
agtgagcgag cgagcgcgca g                                              2241
```

-continued

```
<210> SEQ ID NO 26
<211> LENGTH: 108
<212> TYPE: DNA
<213> ORGANISM: Homo sapiens

<400> SEQUENCE: 26
gaaacaagtt acatcgaaga caactccaat caaaatggtg ctgtatctct gatattctca      60
ctcaaagagg aagttggtgc cctggccaag gtcctgcgct tatttgag               108

<210> SEQ ID NO 27
<211> LENGTH: 49
<212> TYPE: DNA
<213> ORGANISM: Artificial Sequence
<220> FEATURE:
<223> OTHER INFORMATION: ENGINEERED SEQUENCE

<400> SEQUENCE: 27
gaaacaagtt acatcgaaga caactccaat caaaacctgc ttatttgag                49

<210> SEQ ID NO 28
<211> LENGTH: 109
<212> TYPE: DNA
<213> ORGANISM: Artificial Sequence
<220> FEATURE:
<223> OTHER INFORMATION: Engineered sequence

<400> SEQUENCE: 28
gaaacaagtt acatcgaaga caactccaat caaaatggtg ctgtatctct gatattctca      60
ctcaaagagg aagttggtgc cctggtccaa ggtcctgcgc ttatttgag             109

<210> SEQ ID NO 29
<211> LENGTH: 109
<212> TYPE: DNA
<213> ORGANISM: Artificial Sequence
<220> FEATURE:
<223> OTHER INFORMATION: engineered sequence

<400> SEQUENCE: 29
gaaacaagtt acatcgaaga caactccaat caaaaatggt gctgtatctc tgatattctc      60
actcaaagag gaagttggtg ccctggccaa ggtcctgcgc ttatttgag             109

<210> SEQ ID NO 30
<211> LENGTH: 102
<212> TYPE: DNA
<213> ORGANISM: Artificial Sequence
<220> FEATURE:
<223> OTHER INFORMATION: engineered sequence

<400> SEQUENCE: 30
gaaacaagtt acatcgaaga caactccaat ggtgctgtat ctctgatatt ctcactcaaa      60
gaggaagttg gtgccctggc caaggtcctg cgcttatttg ag                   102

<210> SEQ ID NO 31
<211> LENGTH: 108
<212> TYPE: DNA
<213> ORGANISM: Artificial Sequence
<220> FEATURE:
<223> OTHER INFORMATION: Consensus sequence
```

<400> SEQUENCE: 31
gaaacaagtt acatcgaaga caactccaat caaaatggtg ctgtatctct gatattctca        60
ctcaaagagg aagttggtgc cctggccaag gtcctgcgct tatttgag                    108

GENE THERAPY FOR TREATING PHENYLKETONURIA

CROSS-REFERENCE TO RELATED APPLICATIONS

This application is a continuation of U.S. patent application Ser. No. 16/474,960, filed Jun. 28, 2019, which is a National Stage Entry under 35 U.S.C. 371 of International Patent Application No. PCT/US2017/068897, filed Dec. 29, 2017, which claims the benefit of priority of US Provisional Patent Application No. 62/440,651, filed Dec. 30, 2016, US Provisional Patent Application No. 62/469,898, filed Mar. 10, 2017, and US Provisional Patent Application No. 62/505,373, filed May 12, 2017. These applications are incorporated by reference herein.

INCORPORATION-BY-REFERENCE OF MATERIAL SUBMITTED IN ELECTRONIC FORM

Applicant hereby incorporates by reference the Sequence Listing material filed in electronic form herewith. This file is labeled "UPN-16-7939PCT_ST25.txt".

1. INTRODUCTION

The application relates to embodiments useful for a gene therapy for treating phenylketonuria.

2. BACKGROUND

As one of the most common inborn errors of metabolism, Phenylketonuria (PKU) occurs in 1 in 10,000 to 15,000 newborns in the United States. The current treatment approaches require the affected individual to adhere consistently to an unpalatable and expensive dietary restriction and/or take enzyme substitution with phenylalanine ammonia lyase from birth for their whole life.

The most common cause of PKU is deficiency of phenylalanine hydroxylase (PAH) due to a recessively inherited mutation in the PAH gene. PAH is expressed primarily in the liver that catalyzes the irreversible hydroxylation of phenylalanine to tyrosine. Thus, deficiency in PAH affects the catabolic pathway of phenylalanine, resulting in accumulation of phenylalanine. High plasma phenylalanine levels results in build-up of phenylalanine in the brain and can affect brain development and function, resulting in intellectual disability and seizures. Furthermore, reduction of plasma phenylalanine via dietary restriction and enzyme substitution is expensive, inconvenient and has been linked with various adverse complications, such as persistent mild cognitive deficits.

An alternative approach to achieve sustained therapeutic levels of PAH is through continuous in vivo production of the native enzyme in the hepatocytes using gene transfer mediated by a cell-directed adeno-associated virus (AAV) or other viral or non-viral vector. Several attempts of vector-mediated PAH expression have been tested preliminary on mouse studies. See, e.g., Harding et al, Complete correction of hyperphenylalaninemia following liver-directed, recombinant AAV2/8 vector mediated gene therapy in murine phenylketonuria Gene Ther. 2006 March; 13(5):457-6 and Viecelli et al, Treatment of Phenylketonuria Using Mini-circle-Based Naked-DNA Gene Transfer to Murine Liver Hepatology. 2014 September; 60(3): 1035-1043, which are incorporated herein by reference. However, the evaluations of delivery efficiency, immune stimulation, long-term expression stability and safety are either lacking or not optimal. Thus, more efficient AAV.hPAH vectors are needed for PKU treatment.

SUMMARY

The embodiments described herein relate to an AAV gene therapy vector for delivering normal human phenylalanine hydroxylase (PAH) to a subject in need thereof, following intravenous administration of the vector resulting in long-term, perhaps 10 years or more, of clinically meaningful correction of hyperphenylalaninemia. The subject patient population is patients with moderate to severe hyperphenylalaninemia, including those with PKU, variant PKU or non-PKU hyperphenylalaninemia. The intended vector dose is intended to deliver PAH blood levels of approximately 15% or greater as compared to wild type, which is the level which has been reported for "moderate" PKU patients. See, Kaufman, S., PNAS, 96:3160-4 (1999), which is incorporated herein by reference. In another embodiment, the intended vector dose is intended to deliver PAH to result in a reduction of plasma phenylalanine levels by 25% or greater. In one embodiment, the goal for the AAV vector treatment is conversion of severe PKU patients to either moderate or mild PKU thus lessening the burden associated with a severely limited phenylalanine diet.

In one aspect, this application provides the use of a replication deficient adeno-associated virus (AAV) to deliver a human phenylalanine hydroxylase (PAH) gene to liver cells of patients (human subjects) diagnosed with PKU. The recombinant AAV vector (rAAV) used for delivering the hPAH gene ("rAAV.hPAH") should have a tropism for the liver (e.g., a rAAV bearing an AAV8 capsid), and the hPAH transgene should be controlled by liver-specific expression control elements. In one embodiment, the expression control elements include one or more of the following: an enhancer; a promoter; an intron; a WPRE; and a polyA signal. Such elements are further described herein.

In one embodiment, the hPAH coding sequence is shown in SEQ ID NO: 1. In one embodiment, the PAH protein sequence is shown in SEQ ID NO: 2. The coding sequence for hPAH is, in one embodiment, codon optimized for expression in humans. Such sequence may share less than 80% identity to the native hPAH coding sequence (SEQ ID NO: 3). In one embodiment, the hPAH coding sequence is that shown in SEQ ID NO: 1.

In another aspect, provided herein is an aqueous suspension suitable for administration to a PKU patient which includes the rAAV described herein. In some embodiments, the suspension includes an aqueous suspending liquid and about $1\times10^{12}$ to about $1\times10^{14}$ genome copies (GC) of the rAAV/mL. The suspension is, in one embodiment, suitable for intravenous injection. In other embodiment, the suspension further includes a surfactant, preservative, and/or buffer dissolved in the aqueous suspending liquid.

In another embodiment, provided herein is a method of treating a patient having PKU with an rAAV as described herein. In one embodiment, about $1\times10^{11}$ to about $3\times10^{13}$ genome copies (GC) of the rAAV/kg patient body weight are delivered the patient in an aqueous suspension.

3. BRIEF DESCRIPTION OF THE DRAWINGS

FIG. 1 is a schematic representation of pAAV.TBG. PI.hPAHco.WPRE.bGH cis plasmid.

Figure 2A:
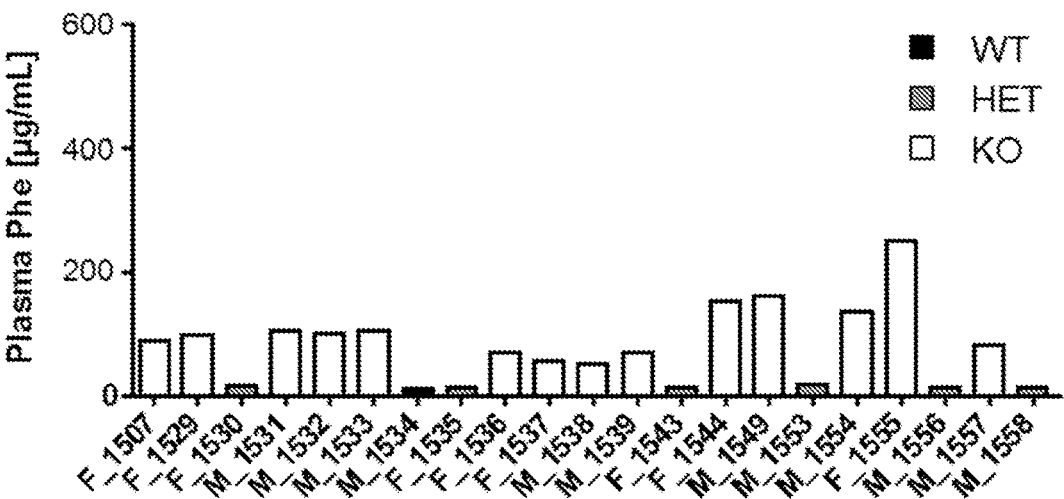
FIG. 2A is a bar graph of plasma phenylalanine (Phe) levels in PAH_KO_A mouse model (shown in white) and wild-type (shown in black) or heterozygous (shown in grey) littermates, as described in Example 1. These results are summarized in FIG. 2D.
Figure 2B:
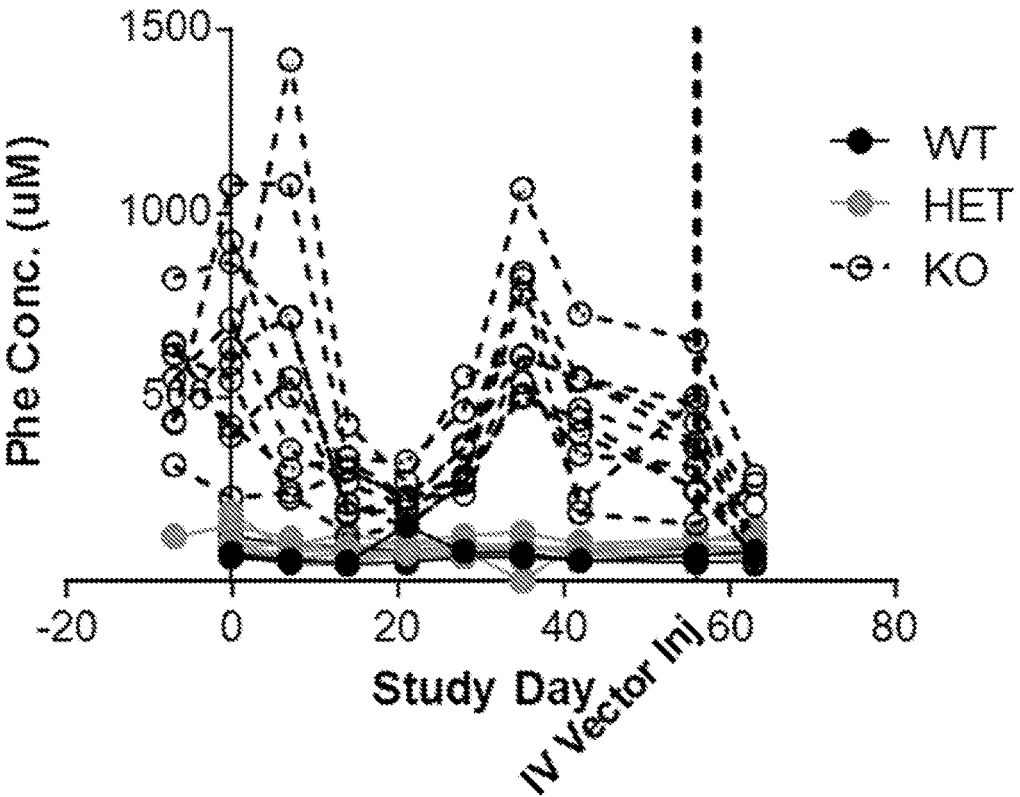

FIG. 2B is a line graph of plasma phenylalanine (Phe) levels in PAH_KO_A mice (shown in white) with heterozygous (shown in grey) and wild-type (shown in black) littermates provided as controls. Mice were injected with $1 \times 10^{13}$ GC/kg or $1 \times 10^{12}$ GC/kg of AAV8.TBG.PI.hPAHco.WPRE.bGH on day 56 of natural history study as described in Example 3. Experiment was performed on 7 male and 3 female PAH_KO_A mice from the natural history study.

Figure 2C:
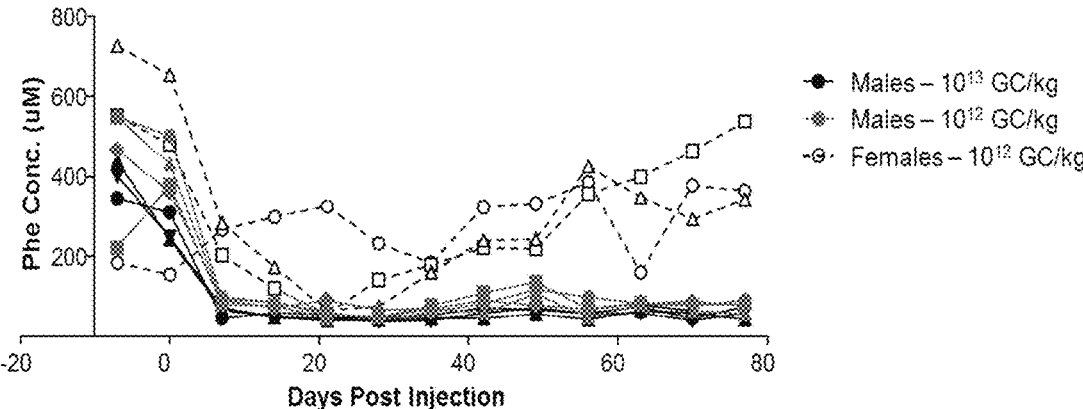

FIG. 2C is a line graph of plasma phenylalanine (Phe) levels in PAH_KO_A mouse model injected with $1 \times 10^{13}$ GC/kg or $1 \times 10^{12}$ GC/kg of AAV8.TBG.PI.hPAHco.WPRE.bGH as described in Example 3. The day of injection was Day 0.

Figure 2D:
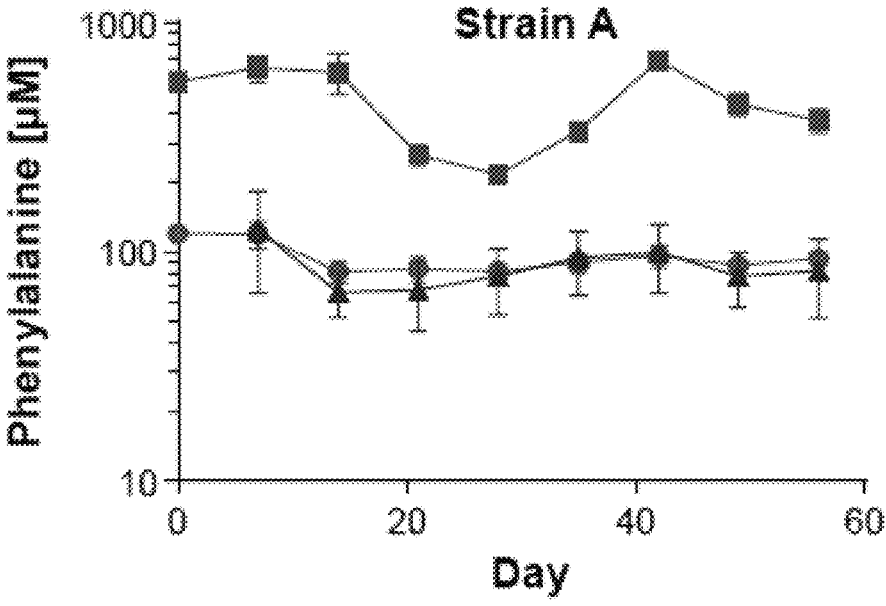

FIG. 2D is a line graph showing the mean Phe levels for the mice studied in FIG. 2A. Values expressed as mean+/−SEM.

Figure 3A:
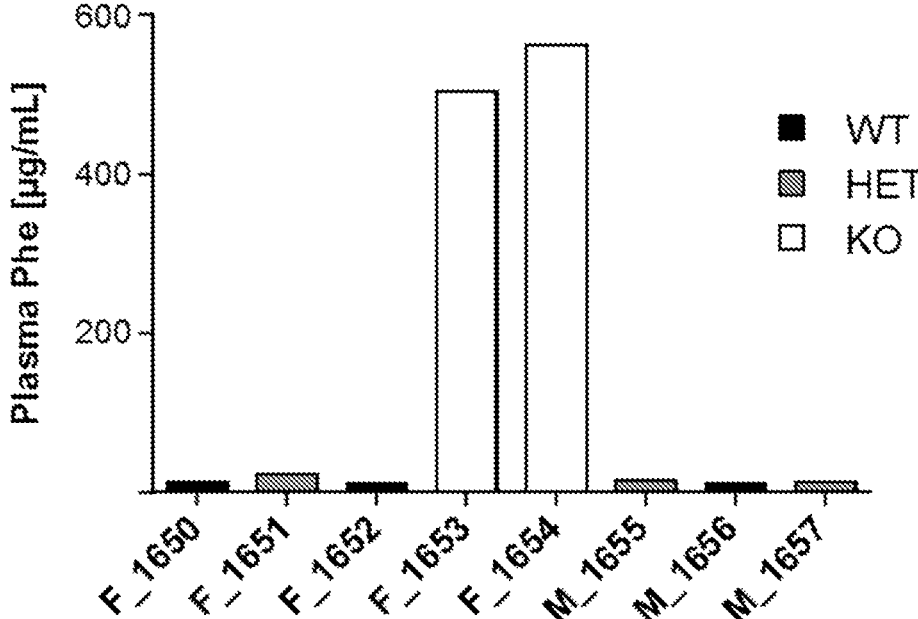

FIG. 3A is a bar graph of plasma phenylalanine (Phe) levels in PAH_KO_B mouse model (shown in white) and wild-type (shown in black) or heterozygous (shown in grey) littermates, as described in Example 1. These results are summarized in FIG. 3D.

Figure 3B:
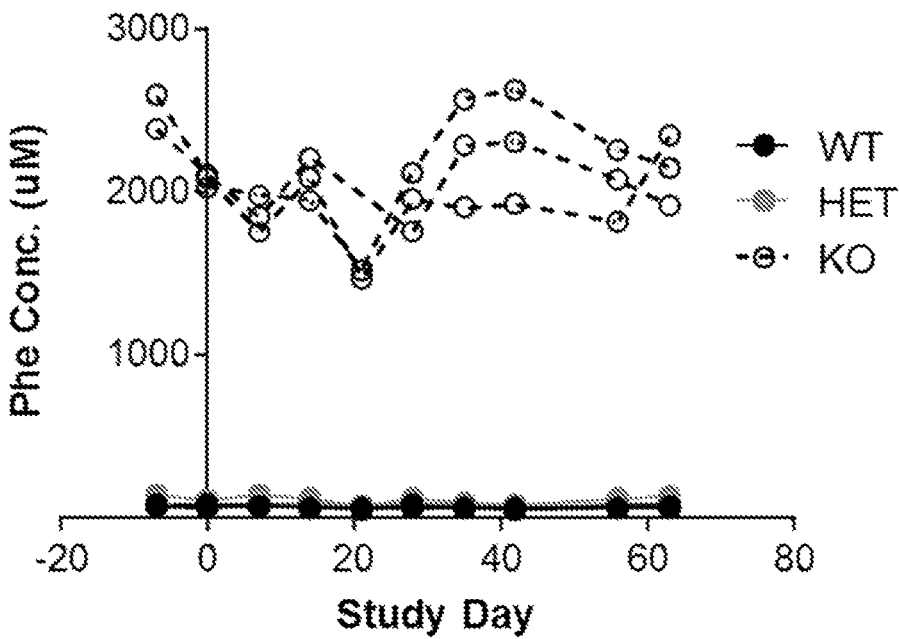

FIG. 3B is a line graph of plasma phenylalanine (Phe) levels in PAH_KO_B mice (shown in white) with heterozygous (shown in grey) and wild-type (shown in black) littermates provided as controls. Experiment was performed on 3 female PAH_KO_B mice from the natural history study.

Figure 3C:
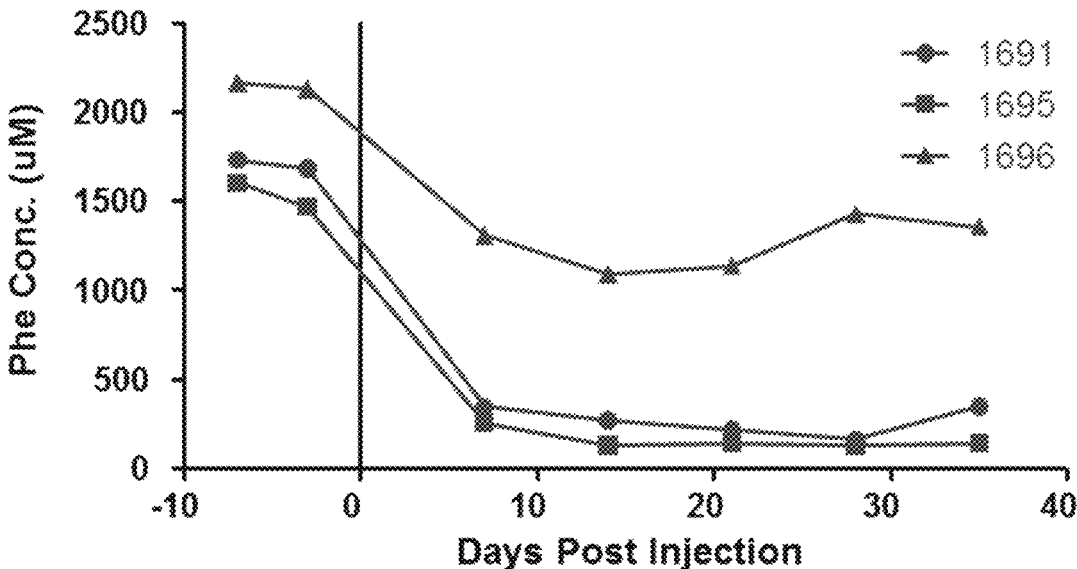

FIG. 3C is a line graph of plasma phenylalanine (Phe) levels in PAH_KO_B mouse model injected with $1 \times 10^{12}$ GC/kg of AAV8.TBG.PI.hPAHco.WPRE.bGH as described in Example 3. Mice Identification Numbers 1691, 1695 and 1696 were females injected with $1 \times 10^{12}$ GC/kg on Day 0.

Figure 3D:
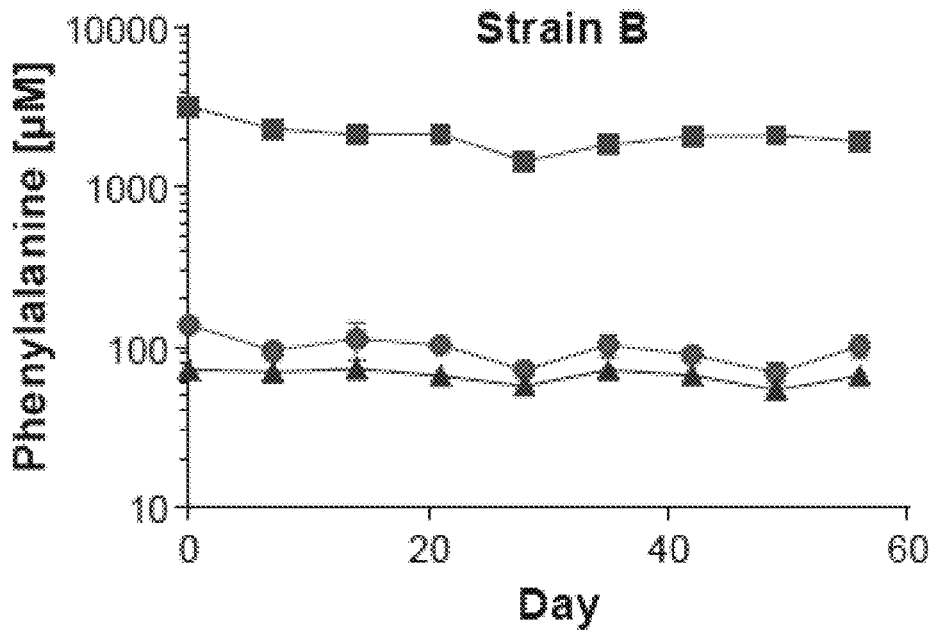
Figure 4A:
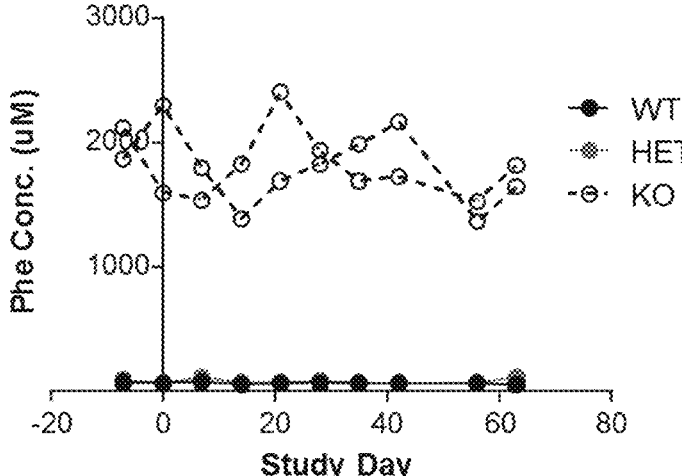

FIG. 3D is a line graph showing the mean Phe levels for the mice studied in FIG. 3A. Values expressed as mean+/−SEM. FIG. 4A is a line graph of plasma phenylalanine (Phe) levels in PAH_KO_C mouse model (shown in white) and wild-type (shown in black) or heterozygous (shown in grey) littermates, as described in Example 1. These results are summarized in FIG. 4C.

Figure 4B:
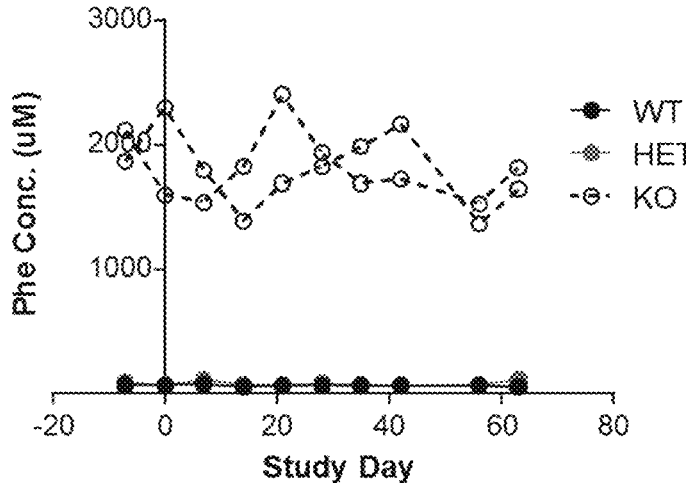

FIG. 4B is a line graph of plasma phenylalanine (Phe) levels in PAH_KO_C mice (shown in white) with heterozygous (shown in grey) and wild-type (shown in black) littermates provided as controls. Experiment was performed on 2 male PAH_KO_C mice from the natural history study.

Figure 4C:
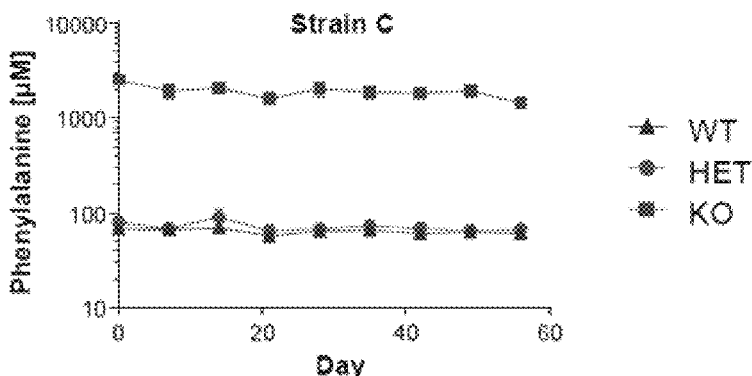

FIG. 4C is a line graph showing the mean Phe levels for the mice studied in FIG. 4A. Values expressed as mean+/−SEM.

Figure 5:
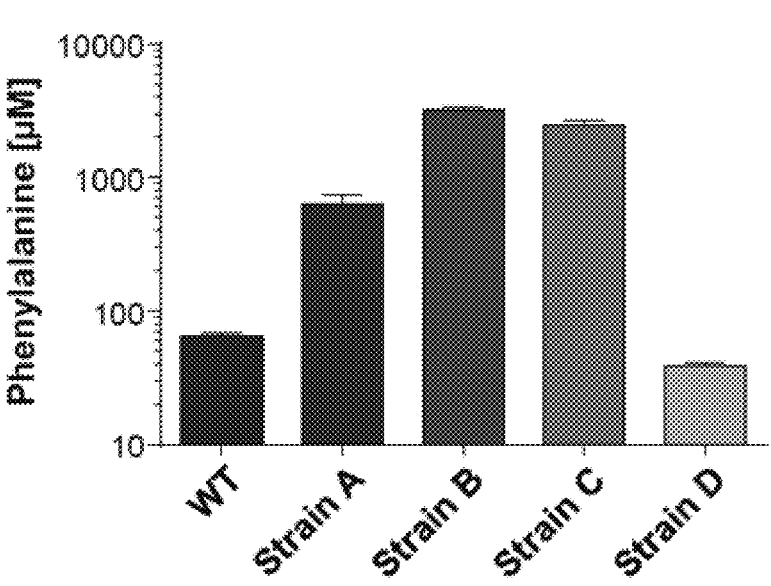

FIG. 5 is a bar graph summarizing the results of FIGS. 2A, 3A and 4A. Plasma phenylalanine (Phe) levels were detected via LC/MS/MS and the data from PAH_KO_A, PAH_KO_B and PAH_KO_C mice bled from 6-8 weeks of age. Plasma was isolated and analyzed for Phe concentration. Wild-type littermates were provided as negative controls.

Figure 6A:
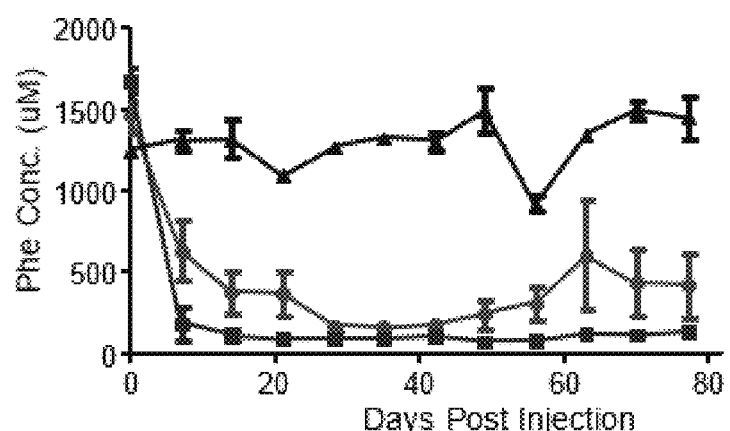
Figure 6B:
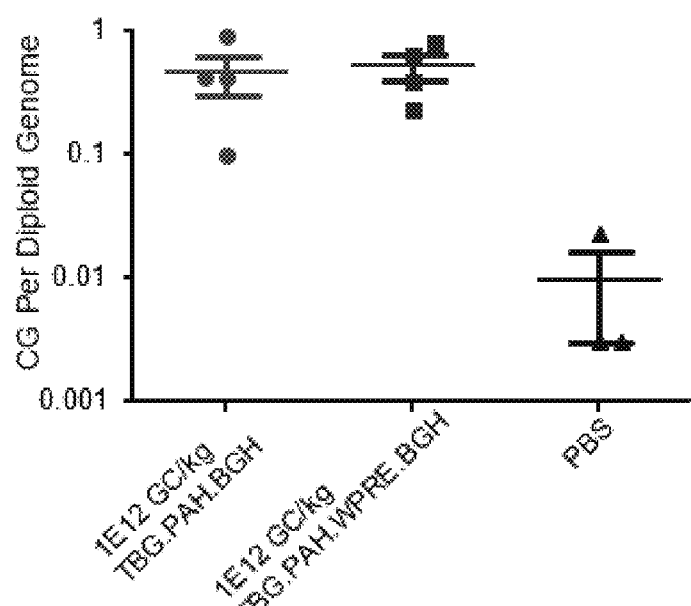
Figure 6C:
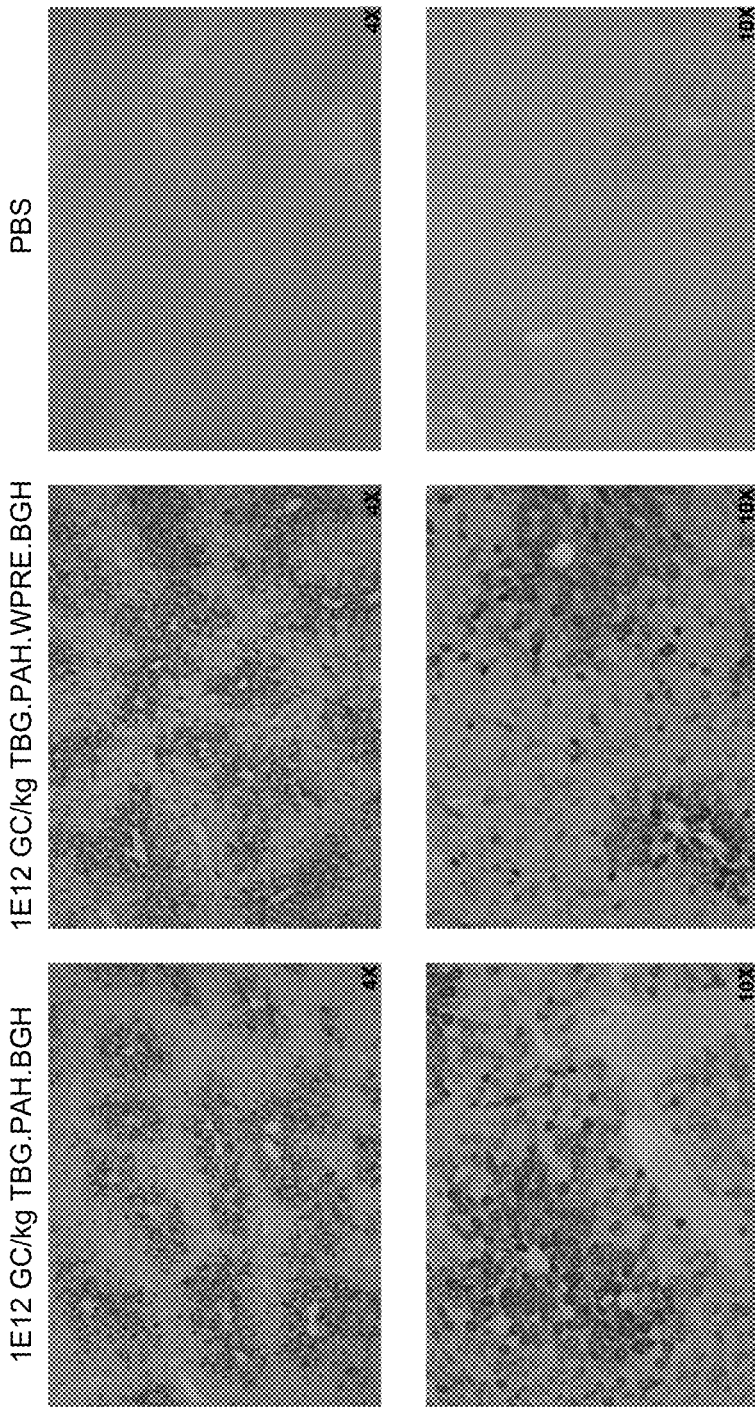

FIG. 6A-6C demonstrate that AAV8.TBG.hPAHco rescues phenylalanine levels in PKU_KO_B mice. PKU B mice ages 17-22 weeks were given either $10^{12}$ GC/kg of either AAV8.TBG.hPAHco.bGH (circles) or AAV8.TBG.hPAHco.WPRE.bGH (squares) after pretreatment phenylalanine levels were established. PBS treatment shown with triangles. Mice were then bled weekly, and plasma was isolated and phenylalanine concentration was determined (A). At the termination of the study, liver was collected and genome copy analysis (B) and immunohistochemistry (C) was performed. Values expressed as mean±SEM.

Figure 7:
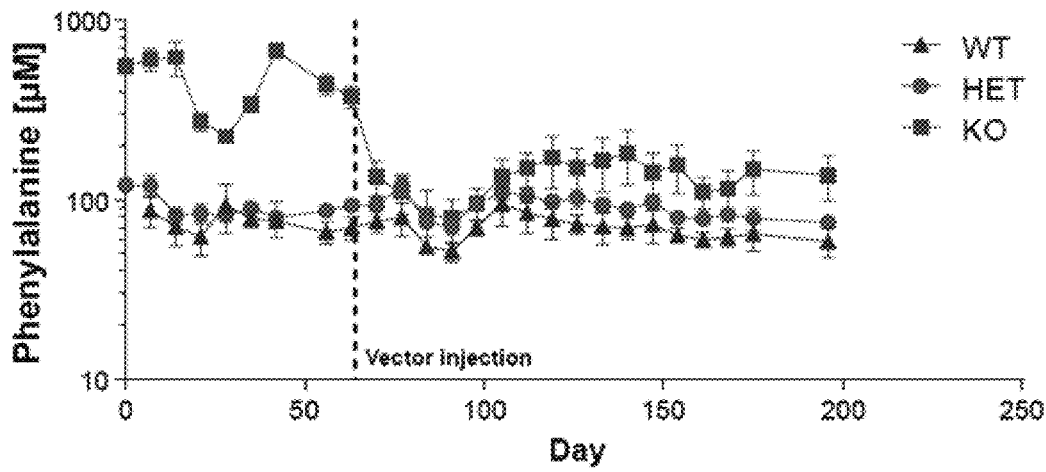

FIG. 7 is a line graph demonstrating that AAV gene therapy lowers plasma Phe concentration in PKU_KO_A mice. WT (triangle), heterozygous (circle) and PKU_KO_A (KO) mice were injected intravenously with $10^{11}$ GC/kg of AAV8.TBG.hPAHco after baseline phenylalanine levels were established. Mice were then bled weekly, and plasma was isolated and analyzed for Phe concentration. Values expressed as mean+/−SEM. Phe levels in plasma decreased by 71% following intravenous administration of AAV8.TBG.hPAHco.

FIGS. 8A-8C demonstrate that high does AAV9.TBG.hPAHco rescues phenylalanine levels in PKU_KO_B mice. PKU_KO_B mice were given either $10^{12}$ GC/kg, $3 \times 10^{11}$ GC/kg, or $10^{11}$ GC/kg, of AAV8.TBG.hPAHco after baseline phenylalanine levels were established. Mice were then bled weekly, and plasma was isolated and analyzed for Phe concentration (A). Values expressed as mean+/−SEM. At termination of the study, liver was collected and genome copy analysis (B) and immunohistochemistry (C) was performed. Protein expression and reduction in Phe levels seen at a dose of $10^{12}$ GC/kg.

Figure 9:
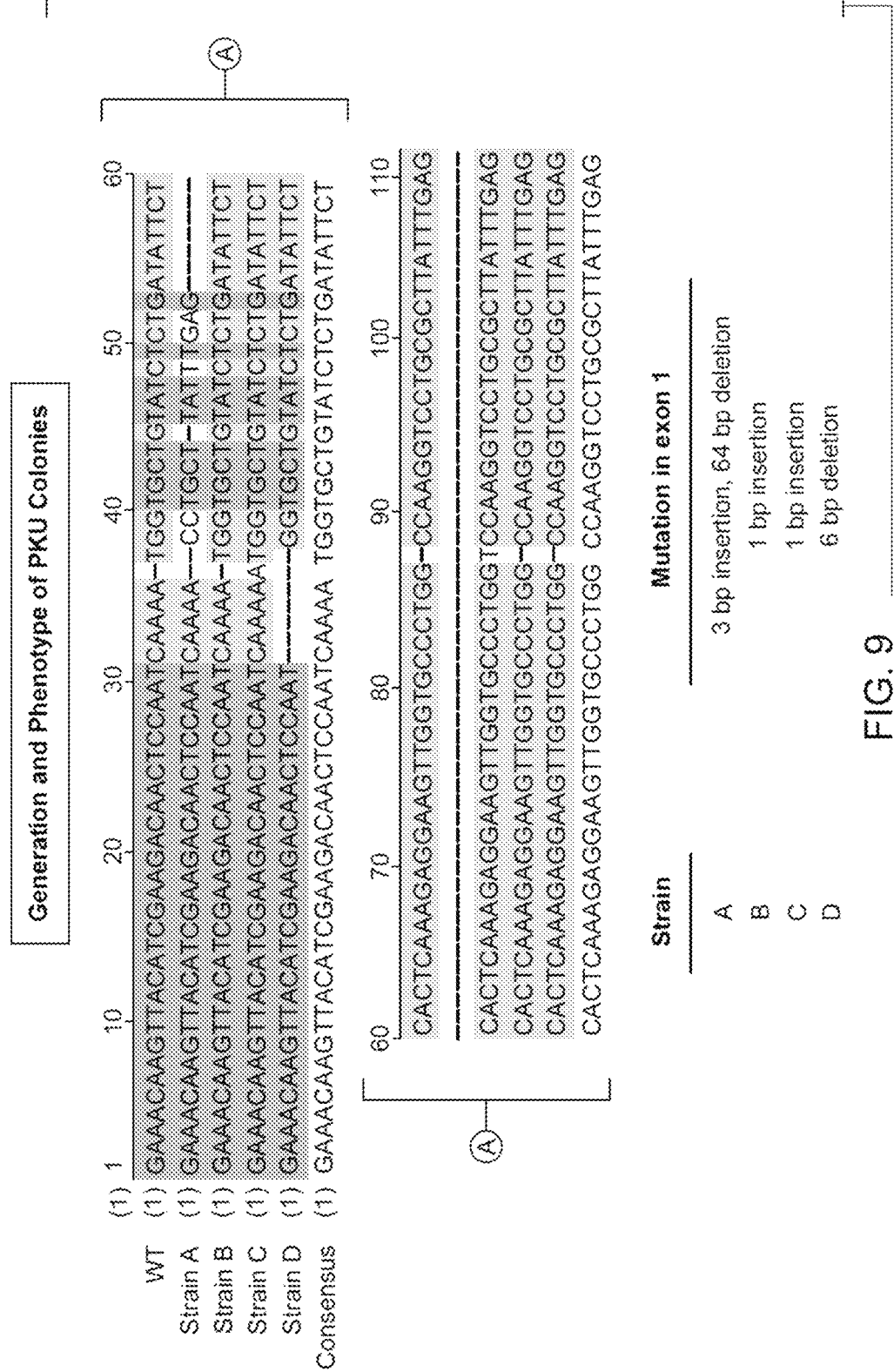

FIG. 9 shows an alignment of a portion of the PAH sequence for wild type (WT), PAH_KO_A (Strain A), PAH_KO_B (Strain B), PAH_KO_C (Strain C), PAH_KO_D (Strain D) and consensus.

4. DETAILED DESCRIPTION

The embodiments described in the application relate to the use of a replication deficient adeno-associated virus (AAV) to deliver a human phenylalanine hydroxylase (PAH) gene to liver cells of patients (human subjects) diagnosed with phenylketonuria (PKU). The recombinant AAV vector (rAAV) used for delivering the hPAH gene ("rAAV.hPAH") should have a tropism for the liver (e.g., a rAAV bearing an AAV8 capsid), and the hPAH transgene should be controlled by liver-specific expression control elements. In one embodiment, the expression control elements include one or more of the following: an enhancer; a promoter; an intron; a WPRE; and a polyA signal. Such elements are further described herein.

As used herein, "AAV8 capsid" refers to the AAV8 capsid having the amino acid sequence of GenBank, accession: YP_077180.1, SEQ ID NO: 19, which is incorporated by reference herein. Some variation from this encoded sequence is permitted, which may include sequences having about 99% identity to the referenced amino acid sequence in YP_077180.1 and WO 2003/052051 (which is incorporated herein by reference) (i.e., less than about 1% variation from the referenced sequence). Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2015/0315612.

As used herein, the term "NAb titer" a measurement of how much neutralizing antibody (e.g., anti-AAV Nab) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199(3): p. 381-390, which is incorporated by reference herein.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 32 amino acids, about 330 amino acids, or a peptide fragment thereof or the corresponding nucleic acid sequence coding sequencers. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

As used herein, the term "operably linked" refers to both expression control sequences that are contiguous with the gene of interest and expression control sequences that act in trans or at a distance to control the gene of interest.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

Unless defined otherwise in this specification, technical and scientific terms used herein have the same meaning as commonly understood by one of ordinary skill in the art and by reference to published texts, which provide one skilled in the art with a general guide to many of the terms used in the present application.

5.1 Gene Therapy Vectors

In one aspect, a recombinant adeno-associated virus (rAAV) vector carrying the human PAH gene is provided for use in gene therapy. The rAAV.hPAH vector should have a tropism for the liver (e.g., a rAAV bearing an AAV8 capsid) and the hPAH transgene should be controlled by liver-specific expression control elements. The vector is formulated in a buffer/carrier suitable for infusion in human subjects. The buffer/carrier should include a component that prevents the rAAV from sticking to the infusion tubing but does not interfere with the rAAV binding activity in vivo.

5.1.1. The rAAV.hPAH Vector

5.1.1.1. The hPAH Sequence

Phenylketonuria is an inherited error of metabolism caused predominantly by mutations in the phenylalanine hydroxylase (PAH) gene. Mutations in the PAH gene result in decreased catalytic activity affecting the catabolic pathway of phenylalanine (Phe). PAH is a hepatic enzyme that requires the cofactor tetrahydrobiopterin ($BH_4$) to convert Phe to tyrosine (Tyr). A deficiency in PAH or its cofactor $BH_4$ results in the accumulation of excess phenylalanine, whose toxic effects can cause severe and irreversible intellectual disability and other disorders, if untreated. See, Havid and Cristodoulou, Transl Pediatr, 2015 October, 4(4): 304-17, which is incorporated herein by reference.

Over 550 mutations of the PAH gene have been described, the majority of which result in deficient enzyme activity. See, Phenylalanine Hydroxylase Locus Knowledgebase, accessed online at pandb.mcgill.ca/, which is incorporated herein by reference. Due to the large number of known PKU mutations, and the autosomal recessive nature of the disease, a wide range of disease severity is seen. The severity of the disease is generally classified by blood phenylalanine levels, which are sometimes classified as classic PKU, moderate or variant PKU, mild PKU, or hyperphenylalaninemia. Based on blood Phe levels at diagnosis, there are 4 levels of PKU severity.

Hyperphenylalaninemia, with Phe levels that are slightly above normal range: 120-600 μmol/L (2-10 mg/dL)

Mild, with the lowest blood Phe levels: 600-900 μmol/L (10-15 mg/dL)

Moderate or variant, with blood Phe levels somewhere in the middle: 900-1200 μmol/L (15-20 mg/dL)

Severe or "classic" PKU, with extremely high blood Phe levels: >1200 μmol/L (20 mg/dL)

The goal of therapies described herein would provide functional PAH enzyme resulting in Phe levels in the 120-600 μmol/L range, e.g., a 25% or greater reduction in plasma Phe levels. In another embodiment, the vector dose is intended to deliver PAH to result in a reduction of plasma phenylalanine levels by 25% or greater. In another embodiment, the vector dose is intended to deliver PAH to result in a reduction of plasma phenylalanine levels by 30% or greater. In another embodiment, the vector dose is intended to deliver PAH to result in a reduction of plasma phenyl-alanine levels by 35% or greater. In another embodiment, the vector dose is intended to deliver PAH to result in a reduction of plasma phenylalanine levels by 40% or greater. In another embodiment, the vector dose is intended to deliver PAH to result in a reduction of plasma phenylalanine levels by 45% or greater. In another embodiment, the vector dose is intended to deliver PAH to result in a reduction of plasma phenylalanine levels by 50% or greater. In another embodiment, the vector dose is intended to deliver PAH to result in a reduction of plasma phenylalanine levels by 60% or greater. In another embodiment, the vector dose is intended to deliver PAH to result in a reduction of plasma phenylalanine levels by 70% or greater. In another embodiment, the vector dose is intended to deliver PAH to result in a reduction of plasma phenylalanine levels by 75% or greater.

In one embodiment, the "subject" or "patient" is a mammalian subject having PKU as described above. It is intended that a patient having PKU of any severity is the intended subject.

In one embodiment, the hPAH gene encodes the hPAH protein shown in SEQ ID NO: 2. Thus, in one embodiment, the hPAH transgene can include, but is not limited to, the sequence provided by SEQ ID NO:1 or SEQ ID NO: 3 which are provided in the attached Sequence Listing, which is incorporated by reference herein. SEQ ID NO: 3 provides the cDNA for native human PAH. SEQ ID NO: 1 provides an engineered cDNA for human PAH, which has been codon optimized for expression in humans (sometimes referred to herein as hPAHco). It is to be understood that reference to hPAH herein may, in some embodiments, refer to the hPAH native or codon optimized sequence. Alternatively or additionally, web-based or commercially available computer programs, as well as service based companies may be used to back translate the amino acid sequences to nucleic acid coding sequences, including both RNA and/or cDNA. See, e.g., backtranseq by EMBOSS, http://www.ebi.ac.uk/Tools/st/; Gene Infinity (http://www.geneinfinity.org/sms-/sms_backtranslation.html); ExPasy (http://www.expasy.org/tools/). It is intended that all nucleic acids encoding the described hPAH polypeptide sequences are encompassed, including nucleic acid sequences which have been optimized for expression in the desired target subject (e.g., by codon optimization).

In one embodiment, the nucleic acid sequence encoding hPAH shares at least 95% identity with the native hPAH coding sequence of SEQ ID NO: 3. In another embodiment, the nucleic acid sequence encoding hPAH shares at least 90, 85, 80, 75, 70, or 65% identity with the native hPAH coding sequence of SEQ ID NO: 3. In one embodiment, the nucleic acid sequence encoding hPAH shares about 78% identity with the native hPAH coding sequence of SEQ ID NO: 3. In one embodiment, the nucleic acid sequence encoding hPAH is SEQ ID NO: 1.

In one embodiment, the PAH coding sequence is optimized for expression in the target subject. Codon-optimized coding regions can be designed by various different methods. This optimization may be performed using methods which are available on-line (e.g., GeneArt,), published methods, or a company which provides codon optimizing services, e.g., as DNA2.0 (Menlo Park, CA). One codon optimizing approach is described, e.g., in International Patent Publication No. WO 2015/012924, which is incorporated by reference herein. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Thermo Fisher Scientific Inc. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

5.1.1.2. The rAAV Vector

Because PAH is natively expressed in the liver, it is desirable to use an AAV which shows tropism for liver. In one embodiment, the AAV supplying the capsid is AAV8. In another embodiment, the AAV supplying the capsid is AAVrh.10. In yet another embodiment, the AAV supplying the capsid is a Clade E AAV. Such AAV include rh.2; rh.10; rh. 25; bb.1, bb.2, pi.1, pi.2, pi.3, rh.38, rh.40, rh.43, rh.49, rh.50, rh.51, rh.52, rh.53, rh.57, rh.58, rh.61, rh.64, hu.6, hu.17, hu.37, hu.39, hu.40, hu.41, hu.42, hu.66, and hu.67. This clade further includes modified rh. 2; modified rh. 58; and modified rh.64. See, WO 2005/033321, which is incorporated herein by reference. However, any of a number of rAAV vectors with liver tropism can be used.

In a specific embodiment described in the Examples, infra, the gene therapy vector is an AAV8 vector expressing an hPAH transgene under control of a thyroxine binding globulin (TBG) promoter referred to as AAV8.TBG.PI.hPAHco.WPRE.bGH. The vector genome for such a vector is shown in SEQ ID NO: 20. In another embodiment, the WPRE is omitted, i.e., AAV8.TBG.PI.hPAHco.bGH. The vector genome for such a vector is shown in SEQ ID NO: 21. The external AAV vector component is a serotype 8, T=1 icosahedral capsid consisting of 60 copies of three AAV viral proteins, VP1, VP2, and VP3, at a ratio of 1:1:10. The capsid contains a single-stranded DNA rAAV vector genome.

In one embodiment, the rAAV.hPAH genome contains an hPAH transgene flanked by two AAV inverted terminal repeats (ITRs). In one embodiment, the hPAH transgene includes one or more of an enhancer, promoter, an intron, a Woodchuck Hepatitis Virus (WHP) Posttranscriptional Regulatory Element (WPRE) (e.g., SEQ ID NO: 15), an hPAH coding sequence, and polyadenylation (polyA) signal. In another embodiment, the hPAH transgene includes one or more of an enhancer, promoter, an intron, an hPAH coding sequence, and polyadenylation (polyA) signal. These control sequences are "operably linked" to the hPAH gene sequences. The expression cassette containing these sequences may be engineered onto a plasmid which is used for production of a viral vector.

The ITRs are the genetic elements responsible for the replication and packaging of the genome during vector production and are the only viral cis elements required to generate rAAV. The minimal sequences required to package the expression cassette into an AAV viral particle are the AAV 5' and 3' ITRs, which may be of the same AAV origin as the capsid, or which of a different AAV origin (to produce an AAV pseudotype). In one embodiment, the ITR sequences from AAV2, or the deleted version thereof (ΔITR), are used. However, ITRs from other AAV sources may be selected. Where the source of the ITRs is from AAV2 and the AAV capsid is from another AAV source, the resulting vector may be termed pseudotyped. Typically, an expression cassette for an AAV vector comprises an AAV 5' ITR, the hPAH coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used. In one embodiment, the 5' ITR is that shown in SEQ ID NO: 16. In one embodiment, the 3' ITR is that shown in SEQ ID NO: 17.

In one embodiment, the expression control sequences include one or more enhancer. In one embodiment, the En34 enhancer is included (34 bp core enhancer from the human apolipoprotein hepatic control region), which is shown in SEQ ID NO: 4. In another embodiment, the EnTTR (100 bp enhancer sequence from transthyretin) is included. Such sequence is shown in SEQ ID NO: 5. See, Wu et al, Molecular Therapy, 16(2):280-289, February 2008, which is incorporated herein by reference. In yet another embodiment, the α1-microglogulin/bikunin precursor enhancer is included. In yet another embodiment, the ABPS (shortened version of the 100 bp distal enhancer from the al-microglogulin/bikunin precursor [ABP] to 42 bp) enhancer is included. Such sequence is shown in SEQ ID NO: 6. In yet another embodiment, the ApoE enhancer is included. Such sequence is shown in SEQ ID NO: 7. In another embodiment, more than one enhancer is present. Such combination may include more than one copy of any of the enhancers described herein, and/or more than one type of enhancer.

Expression of the hPAH coding sequence is driven from a liver-specific promoter. An illustrative plasmid and vector described herein uses the thyroxine binding globulin (TBG) promoter (SEQ ID NO: 9), or a modified version thereof. One modified version of the TBG promoter is a shortened version, termed TBG-S1. A modified thyroxine binding globulin (TBG-S1) promoter sequence is shown in SEQ ID NO: 8. Alternatively, other liver-specific promoters may be used such as the transthyretin promoter. Another suitable promoter is the alpha 1 anti-trypsin (A1AT) promoter, or a modified version thereof (which sequence is shown in SEQ ID NO: 10). Another suitable promoter is the TTR promoter (SEQ ID NO: 11). Other suitable promoters include human albumin (Miyatake et al., J. Virol., 71:5124 32 (1997)), humAlb; the Liver Specific promoter (LSP), and hepatitis B virus core promoter, (Sandig et al., Gene Ther., 3:1002 9 (1996). See, e.g., The Liver Specific Gene Promoter Database, Cold Spring Harbor, available online at rulai.schl.edu/LSPD, which is incorporated by reference. Although less desired, other promoters, such as viral promoters, constitutive promoters, regulatable promoters [see, e.g., WO 2011/126808 and WO 2013/04943], or a promoter responsive to physiologic cues may be used may be utilized in the vectors described herein.

In addition to a promoter, an expression cassette and/or a vector may contain other appropriate transcription initiation, termination, enhancer sequences, and efficient RNA processing signals. Such sequences include splicing and polyadenylation (polyA) signals; regulatory elements that enhance expression (i.e., WPRE (SEQ ID NO: 15)); sequences that stabilize cytoplasmic mRNA; sequences that enhance translation efficiency (i.e., Kozak consensus sequence); sequences that enhance protein stability; and when desired, sequences that enhance secretion of the encoded product. In one embodiment, a polyadenylation (polyA) signal is included to mediate termination of hPAH mRNA transcripts. Examples of other suitable polyA sequences include, e.g., bovine growth hormone (SEQ ID NO: 12), SV40, rabbit beta globin, and TK polyA, amongst others.

In one embodiment, the regulatory sequences are selected such that the total rAAV vector genome is about 2.0 to about 5.5 kilobases in size. In one embodiment, the regulatory sequences are selected such that the total rAAV vector genome is about 3.4 kb, about 2.9 kb, about 3.3 kb, about 2.2 kb or about 2.5 kb in size. In one embodiment, it is desirable that the rAAV vector genome approximate the size of the native AAV genome. Thus, in one embodiment, the regulatory sequences are selected such that the total rAAV vector genome is about 4.7 kb in size. In another embodiment, the total rAAV vector genome is less about 5.2 kb in size. The size of the vector genome may be manipulated based on the size of the regulatory sequences including the promoter, enhancer, intron, poly A, etc. See, Wu et al, Mol Ther, January 2010 18(1):80-6, which is incorporated herein by reference.

Thus, in one embodiment, an intron is included in the vector. Suitable introns include the human beta globin IVS2 (SEQ ID NO: 13). See, Kelly et al, Nucleic Acids Research, 43(9):4721-32 (2015), which is incorporated herein by reference. Another suitable promoter includes the Promega chimeric intron (SEQ ID NO: 14), sometimes referred to as "PI"). See, Almond, B. and Schenborn, E. T. A Comparison of pCI-neo Vector and pcDNA4/HisMax Vector. [Internet] 2000, which is incorporated herein by reference. Available from: www.promega.com/resources/pubhub/enotes/a-comparison-of-pcineo-vector-and-pcdna4hismax-vector/). Another suitable intron includes the hFIX intron (SEQ ID NO: 18). Various introns suitable herein are known in the art and include, without limitation, those found at http://bpg.u-toledo.edu/~afedorov/lab/eid.html, which is incorporated herein by reference. See also, Shepelev V., Fedorov A. Advances in the Exon-Intron Database. Briefings in Bioinformatics 2006, 7: 178-185, which is incorporated herein by reference.

In one embodiment, the rAAV vector genome comprises SEQ ID NO: 20, SEQ ID NO: 21, SEQ ID NO:22, SEQ ID NO: 23, SEQ ID NO: 24 or SEQ ID NO:25.

5.1.2. Compositions

In one embodiment, the rAAV.hPAH virus is provided in a pharmaceutical composition which comprises an aqueous carrier, excipient, diluent or buffer. In one embodiment, the buffer is PBS. In a specific embodiment, the rAAV.hPAH formulation is a suspension containing an effective amount of rAAV.hPAH vector suspended in an aqueous solution containing 0.001% Pluronic F-68 in TMN200 (200 mM sodium chloride, 1 mM magnesium chloride, 20 mM Tris, pH 8.0). However, various suitable solutions are known including those which include one or more of: buffering saline, a surfactant, and a physiologically compatible salt or mixture of salts adjusted to an ionic strength equivalent to about 100 mM sodium chloride (NaCl) to about 250 mM sodium chloride, or a physiologically compatible salt adjusted to an equivalent ionic concentration.

For example, a suspension as provided herein may contain both NaCl and KCl. The pH may be in the range of 6.5 to 8.5, or 7 to 8.5, or 7.5 to 8. A suitable surfactant, or combination of surfactants, may be selected from among Poloxamers, i.e., nonionic triblock copolymers composed of a central hydrophobic chain of polyoxypropylene (poly (propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension. In another embodiment, the vector is suspended in an aqueous solution containing 180 mM sodium chloride, 10 mM sodium phosphate, 0.001% Poloxamer 188, pH 7.3.

In one embodiment, the formulation is suitable for use in human subjects and is administered intravenously. In one embodiment, the formulation is delivered via a peripheral vein by bolus injection. In one embodiment, the formulation is delivered via a peripheral vein by infusion over about 10 minutes (±5 minutes). In one embodiment, the formulation is delivered via a peripheral vein by infusion over about 20 minutes (±5 minutes). In one embodiment, the formulation is delivered via a peripheral vein by infusion over about 30 minutes (±5 minutes). In one embodiment, the formulation is delivered via a peripheral vein by infusion over about 60 minutes (±5 minutes). In one embodiment, the formulation is delivered via a peripheral vein by infusion over about 90 minutes (±10 minutes). However, this time may be adjusted as needed or desired. Any suitable method or route can be used to administer an AAV-containing composition as described herein, and optionally, to co-administer other active drugs or therapies in conjunction with the AAV-mediated delivery of hPAH described herein. Routes of administration include, for example, systemic, oral, inhalation, intranasal, intratracheal, intraarterial, intraocular, intravenous, intramuscular, subcutaneous, intradermal, and other parental routes of administration.

In one embodiment, the formulation may contain, e.g., about $1.0\times10^{11}$ genome copies per kilogram of patient body weight (GC/kg) to about $1\times10^{15}$ GC/kg, about $5\times10^{11}$ genome copies per kilogram of patient body weight (GC/kg) to about $3\times10^{13}$ GC/kg, or about $1\times10^{12}$ to about $1\times10^{14}$ GC/kg, as measured by oqPCR or digital droplet PCR (ddPCR) as described in, e.g., M. Lock et al, Hum Gene Ther Methods. 2014 April; 25(2):115-25. doi: 10.1089/hgtb.2013.131. Epub 2014 Feb. 14, which is incorporated herein by reference. In one embodiment, the rAAV.hPAH formulation is a suspension containing at least $1\times10^{13}$ genome copies (GC)/mL, or greater, as measured by oqPCR or digital droplet PCR (ddPCR) as described in, e.g., M. Lock et al, supra.

In order to ensure that empty capsids are removed from the dose of AAV.hPAH that is administered to patients, empty capsids are separated from vector particles during the vector purification process, e.g., using the method discussed herein. In one embodiment, the vector particles containing packaged genomes are purified from empty capsids using the process described in U.S. Patent Appln No. 62/322,098, filed on Apr. 13, 2016, and entitled "Scalable Purification Method for AAV8", which is incorporated by reference herein. Briefly, a two-step purification scheme is described which selectively captures and isolates the genome-containing rAAV vector particles from the clarified, concentrated supernatant of a rAAV production cell culture. The process utilizes an affinity capture method performed at a high salt concentration followed by an anion exchange resin method performed at high pH to provide rAAV vector particles which are substantially free of rAAV intermediates. Similar purification methods can be used for vectors having other capsids.

While any conventional manufacturing process can be utilized, the process described herein (and in U.S. Patent Appln No. 62/322,098) yields vector preparations wherein between 50 and 70% of the particles have a vector genome, i.e., 50 to 70% full particles. Thus for an exemplary dose of $1.6\times10^{12}$ GC/kg, and the total particle dose will be between $2.3\times10^{12}$ and $3\times10^{12}$ particles. In another embodiment, the proposed dose is one half log higher, or $5\times10^{12}$ GC/kg, and the total particle dose will be between $7.6\times10^{12}$ and $1.1\times10^{13}$ particles. In one embodiment, the formulation is be characterized by an rAAV stock having a ratio of "empty" to "full" of 1 or less, preferably less than 0.75, more preferably, 0.5, preferably less than 0.3.

A stock or preparation of rAAV8 particles (packaged genomes) is "substantially free" of AAV empty capsids (and other intermediates) when the rAAV8 particles in the stock are at least about 75% to about 100%, at least about 80%, at least about 85%, at least about 90%, at least about 95%, or at least 99% of the rAAV8 in the stock and "empty capsids" are less than about 1%, less than about 5%, less than about 10%, less than about 15% of the rAAV8 in the stock or preparation.

Generally, methods for assaying for empty capsids and AAV vector particles with packaged genomes have been known in the art. See, e.g., Grimm et al., *Gene Therapy* (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., J. Virol. (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturer's instructions. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied. Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is provided herein which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April; 25(2):115-25. doi: 10.1089/hgtb.2013.131. Epub 2014 Feb. 14.

5.2 Patient Population

As discussed above, a subject having PKU of any severity is the intended recipient of the compositions and methods described herein.

Subjects may be permitted to continue their standard of care treatment(s) (e.g., diet low in Phe; treatment with sapropterin dihydrochloride) prior to and concurrently with the gene therapy treatment at the discretion of their caring physician. In the alternative, the physician may prefer to stop standard of care therapies prior to administering the gene therapy treatment and, optionally, resume standard of care treatments as a co-therapy after administration of the gene therapy.

Desirable endpoints of the gene therapy regimen are an increase in PAH activity resulting in Phe levels between 120-360 μmol/L. In another embodiment, the vector dose is intended to deliver PAH to result in a reduction of plasma phenylalanine levels by 25% or greater. In another embodiment, the desirable endpoint is reducing plasma Phe levels to take subject to a "moderate" phenotype from a "severe" phenotype. Methods for measurement of phenylalanine levels are known in the art e.g., as described in Gregory et al, Blood phenylalanine monitoring for dietary compliance among patients with phenylketonuria: comparison of methods, Genetics in Medicine (November 2007) 9, 761-765, which is incorporated herein by reference. In one embodiment, patients achieve desired circulating PAH levels after treatment with rAAV.hPAH, alone and/or combined with the use of adjunctive treatments.

5.3. Dosing & Route of Administration

In one embodiment, the rAAV.hPAH vector is delivered as a single dose per patient. In one embodiment, the subject is delivered the minimal effective dose (MED) (as determined by preclinical study described in the Examples herein). As used herein, MED refers to the rAAV.hPAH dose required to achieve PAH activity resulting in Phe levels between 120-360 μmol/L.

As is conventional, the vector titer is determined on the basis of the DNA content of the vector preparation. In one embodiment, quantitative PCR or optimized quantitative PCR as described in the Examples is used to determine the DNA content of the rAAV.hPAH vector preparations. In one embodiment, digital droplet PCR as described in the Examples is used to determine the DNA content of the rAAV.hPAH vector preparations. In one embodiment, the dosage is about $1 \times 10^{11}$ genome copies (GC)/kg body weight to about $1 \times 10^{13}$ GC/kg, inclusive of endpoints. In one embodiment, the dosage is $5 \times 10^{11}$ GC/kg. In another embodiment, the dosage is $5 \times 10^{12}$ GC/kg. In specific embodiments, the dose of rAAV.hPAH administered to a patient is at least $5 \times 10^{11}$ GC/kg, $1 \times 10^{12}$ GC/kg, $1.5 \times 10^{12}$ GC/kg, $2.0 \times 10^{12}$ GC/kg, $2.5 \times 10^{12}$ GC/kg, $3.0 \times 10^{12}$ GC/kg, $3.5 \times 10^{12}$ GC/kg, $4.0 \times 10^{12}$ GC/kg, $4.5 \times 10^{12}$ GC/kg, $5.0 \times 10^{12}$ GC/kg, $5.5 \times 10^{12}$ GC/kg, $6.0 \times 10^{12}$ GC/kg, $6.5 \times 10^{12}$ GC/kg, $7.0 \times 10^{12}$ GC/kg, or $7.5 \times 10^{12}$ GC/kg. Also, the replication-defective virus compositions can be formulated in dosage units to contain an amount of replication-defective virus that is in the range of about $1.0 \times 10^{9}$ GC to about $1.0 \times 10^{15}$ GC. As used herein, the term "dosage" can refer to the total dosage delivered to the subject in the course of treatment, or the amount delivered in a single (of multiple) administration.

In one embodiment, the dosage is sufficient to decrease plasma Phe levels in the patient by 25% or more.

In some embodiments, rAAV.hPAH is administered in combination with one or more therapies for the treatment of PKU, such as a low Phe diet or administration of sapropterin dihydrochloride.

5.4. Measuring Clinical Objectives

Measurements of efficacy of treatment can be measured by transgene expression and activity as determined by plasma Phe levels and/or PAH activity. Further assessment of efficacy can be determined by clinical assessment of dietary Phe tolerance.

As used herein, the rAAV.hPAH vector herein "functionally replaces" or "functionally supplements" the patients defective PAH with active PAH when the patient expresses a sufficient level of PAH to achieve PAH activity resulting in Phe levels between 120-360 µmol/L.

The following examples are illustrative only and are not intended to limit the present invention.

EXAMPLES

The following examples are illustrative only and are not intended to limit the present invention.

Example 1: Mouse Models of Phenylketonuria (PKU)

PAH$^{-/-}$ mice were generated by CRISPR/Cas9 technology at Jackson Labs. Wild-type C57BL/6 mice were injected with Cas9 mRNA and two guide RNAs (sgRNA) targeting the second coding exon of PAH gene directly into mouse zygotes. Mice that developed from these embryos were sequenced to determine the mutation(s) and then bred with C57BL/6J mice to transmit the allele and confirm germline transmission.

Four different mutations were generated and the mice strains were designated as PAH_KO_A, PAH_KO_B, PAH_KO_C, and PAH_KO_D. PAH_KO_A mice demonstrated a 3-bp substitution followed by a 64-bp deletion from the 6534 nt to the 6600 nt of Mus musculus PAH gene [NC_000076.6]. PAH_KO_B and PAH_KO_C mice showed a single base pair insertion after the 6589 nt and the 6539 nt respectively. PAH_KO_D showed a 6 bp deletion from the 6535 nt to the 6540 nt. FIG. 9 shows an alignment of a portion of the PAH sequence for wild type, PAH_KO_A, PAH_KO_B, PAH_KO_C, PAH_KO_D and consensus. A natural history study of these mice was performed. Blood samples were collected via retro orbital or submandibular bleeding. Plasma phenylalanine (Phe) levels were detected via LC/MS/MS and the data from PAH_KO_A, PAH_KO_B and PAH_KO_C mice was acquired and presented in FIGS. 2A, 3A and 4A respectively, and summarized in FIG. 5A. Heterozygous and wild-type littermates were provided as negative controls. Compared to the controls, the plasma phenylalanine levels in PAH_KO_A, PAH_KO_B and PAH_KO_C mice were significantly higher, indicating a functionally deficient PAH in these mice. It also suggested that PAH_KO_A, PAH_KO_B, and PAH_KO_C mice could serve as mouse models for Phenylketonuria (PKU) in human.

However, the fourth knock-out mice, PAH_KO_D, did not exhibit an elevated plasma phenylalanine level and thus excluded from further analysis.

Example 2: AAV Vectors Containing hPAH-AAV8.TBG.PI.hPAHco.WPRE.bGH

Figure 1:
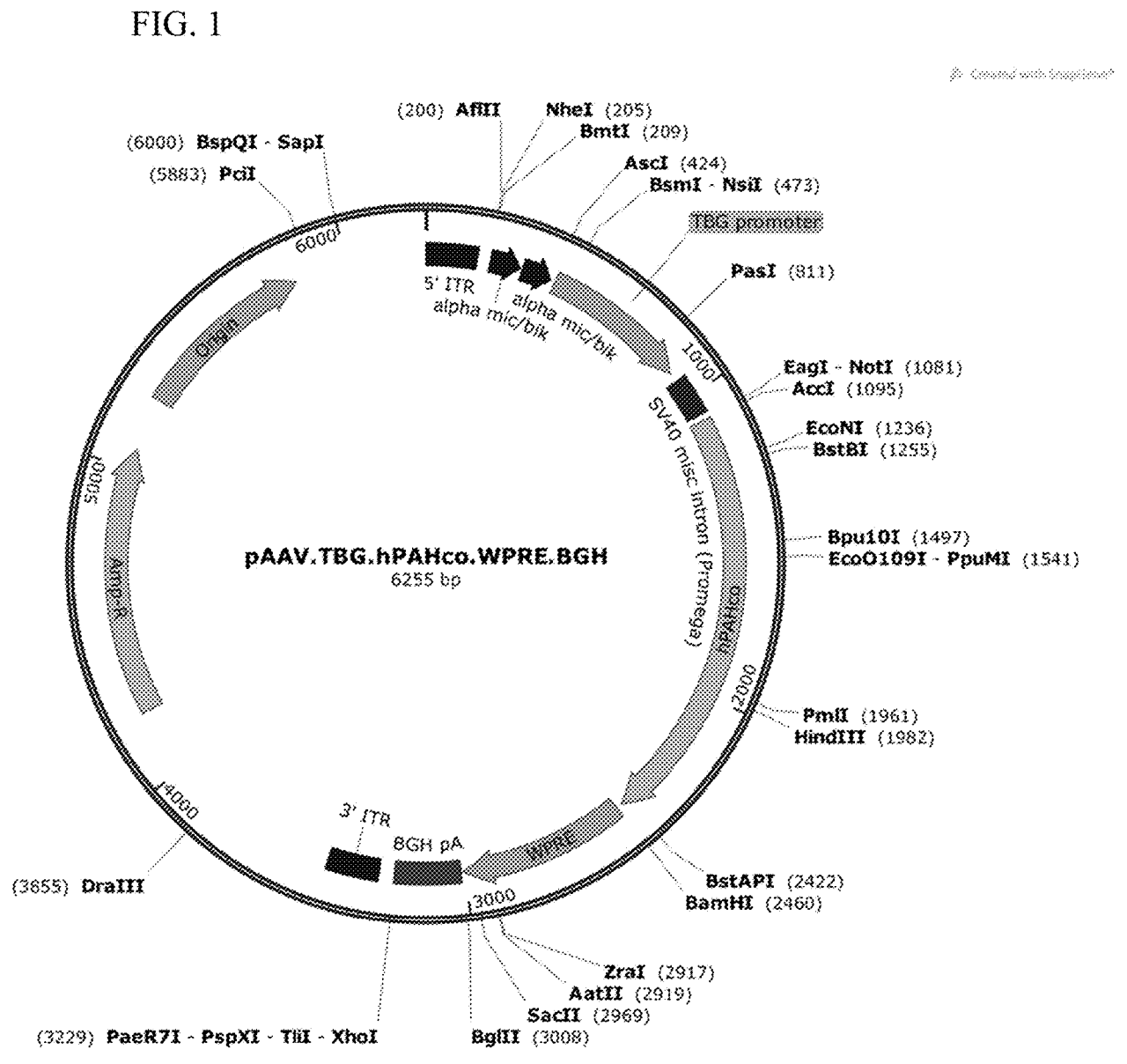

The gene therapy vector AAV8.TBG.PI.hPAHco.WPRE.bGH was constructed by an AAV8 vector bearing a codon-optimized human PAH cDNA under the control of TBG, a hybrid promoter based on the human thyroid hormone-binding globulin promoter and microglobin/bikunin enhancer (FIG. 1). The PAH expression cassette was flanked by AAV2 derived inverted terminal repeats (ITRs) and the expression was driven by a hybrid of the TBG enhancer/promoter and the Woodchuck Hepatitis Virus (WHP) posttranscriptional regulatory element (WPRE) as an enhancer. The transgene also included the Promega SV40 misc intron (PI) and a bovine growth hormone polyadenylation signal (bGH). The vector genome sequence is shown in SEQ ID NO: 20.

The vector was prepared using conventional triple transfection techniques in 293 cells as described e.g., by Mizukami, Hiroaki, et al. *A Protocol for AAV vector production and purification*. Diss. Di-vision of Genetic Therapeutics, Center for MolecularMedicine, 1998., which is incorporated herein by reference. All vectors were produced by the Vector Core at the University of Pennsylvania as previously described [Lock, M., et al, Hum Gene Ther, 21: 1259-1271 (2010)].

Example 3: AAV8.hPAH Vectors in the Model of PKU

All animal procedures were performed in accordance with protocols approved by the Institutional Animal Care and Use Committee (IACUC) of the University of Pennsylvania.

Twenty PAH_KO_A mice were generated. Seven males and three females were assessed in natural history study. On Day 56 of natural history study, three male mice with Identification Number 1531, 1532 and 1533 were injected intravenously via the tail vein with $1\times10^{13}$ GC/kg of the AAV8.TBG.PI.hPAHco.WPRE.bGH vector. Four male mice with Identification Number 1538, 1539, 1554 and 1564 were injected with $1\times10^{12}$ GC/kg of the vector. Three female mice with Identification Number 1507, 1536 and 1537 were injected with $1\times10^{12}$ GC/kg of the vector. The blood samples were collected weekly to evaluate plasma phenylalanine concentration (FIG. 2B). A higher level of phenylalanine was detected in the PAH_KO_A mice before injection compared to the littermate controls, indicating a deficient PAH in PAH_KO_A mice. 7 days after the vector injection, the plasma phenylalanine level of PAH_KO_A mice decreased while the controls remained stable. This result demonstrated that a single injection of AAV8.TBG.PI.hPAHco.WPRE.bGH into PAH_KO_A mice could rescue the deficient PAH and reduce the pathological accumulation of phenylalanine in the blood.

The effects of gender differences and the two doses of the AAV8.TBG.PI.hPAHco.WPRE.bGH vectors were further evaluated in PAH_KO_A mice (FIG. 2C). Plasma phenylalanine levels were observed every week for 11 weeks, e.g, as described in Gregory et al, Blood phenylalanine monitoring for dietary compliance among patients with phenylketonuria: comparison of methods, Genetics in Medicine (November 2007) 9, 761-765, which is incorporated herein by reference. Two of three female mice received $1\times10^{12}$ GC/kg of the vectors and all seven male ones with both doses at $1\times10^{12}$ GC/kg and $1\times10^{13}$ GC/kg displayed a reduced phenylalanine concentration in the plasma. The phenylalanine of the seven male mice maintained at comparably low levels for the 11-week observation period while all three female ones demonstrated a slow increase in plasma phenylalanine level.

Three female PAH_KO_B mice were generated and exanimated in a natural history study. Weekly bleeds for phenylalanine levels were performed and the result confirmed an abnormal accumulation of phenylalanine in the blood compared to the healthy littermate controls. Upon intravenous injection of $1\times10^{12}$ GC/kg of AAV8.TBG.PI.hPAHco.WPRE.bGH, a decreased phenylalanine level was observed in all three females and the low level maintained during the 8-week observation period after the injection.

Two male PAH_KO_C mice were generated for this study and utilized in natural history study. A weekly collection of blood samples were performed and the phenylalanine concentration was assessed. The data showed that during the 9-week observation, both PAH_KO_C mice and the heterozygous/wild-type littermates maintained a comparably stable concentration of plasma phenylalanine while the knock-out mice demonstrated a significantly higher level.

A further study of expression and enzyme activity of PAH in the injected $PAH^{-/-}$ mice was performed. Livers are collected from PAH_KO_A, PAH_KO_B and PAH_KO_C mice injected with vectors or PBS only as well as the healthy littermate controls. mRNA is extracted from the liver and the expression of human PAH is evaluated via RT-PCR. To determine the protein expression of PAH, liver lysates are prepared for detection by western blot while liver sections are prepared for immunohistochemistry. Experiments are also performed to assess the PAH enzyme activity of the $PAH^{-/-}$ mice treated with the vector as well as controls.

To fully evaluate gender difference in all three $PAH^{-/-}$ mice, PAH_KO_A, PAH_KO_B and PAH_KO_C mice were bred to assess the plasma phenylalanine concentration, the expression of PAH on both mRNA and protein level and the enzyme activity of PAH before and after the injection of AAV8.TBG.PI.hPAHco.WPRE.bGH.

To determine the dose-dependent expression of AAV8.TBG.PI.hPAHco.WPRE.bGH and the potential toxicity of the highest dose, various doses of AAV8.TBG.PI.hPAHco.WPRE.bGH are injected into the $PAH^{-/-}$ mice and further assessment of phenylalanine accumulation and PAH expression/activity are performed.

Similar experiments were performed with AAV8.TBG.hPAHco.bGH. PKU B mice ages 17-22 weeks were given either $10^{12}$ GC/kg of either AAV8.TBG.hPAHco.bGH or AAV8.TBG.hPAHco.WPRE.bGH (or PBS for control) after pretreatment phenylalanine levels were established. Mice were then bled weekly, and plasma was isolated and phenylalanine concentration was determined (FIG. 6A). At the termination of the study, liver was collected and genome copy analysis (FIG. 6B) and immunohistochemistry (FIG. 6C) was performed. Phenylalanine levels were reduced in both AAV8.TBG.hPAHco.bGH and AAV8.TBG.hPAHco.WPRE.bGH treated mice.

Further studies were performed with AAV8.TBG.hPAHco.bGH vector. Wildtype, heterozygous (circle) and PKU_KO_A (KO) mice were injected intravenously with $10^{11}$ GC/kg of AAV8.TBG.hPAHco after baseline phenylalanine levels were established. Mice were then bled weekly, and plasma was isolated and analyzed for Phe concentration. Phe levels in plasma decreased by 71% following intravenous administration of AAV8.TBG.hPAHco. FIG. 7.

PKU_KO_B mice were given either $10^{12}$ GC/kg, $3\times10^{11}$ GC/kg, or $10^{11}$ GC/kg, of AAV8.TBG.hPAHco after baseline phenylalanine levels were established. Mice were then bled weekly, and plasma was isolated and analyzed for Phe concentration. At termination of the study, liver was collected and genome copy analysis and immunohistochemistry was performed. Protein expression and reduction in Phe levels were seen at a dose of $10^{12}$ GC/kg.

Meanwhile, administration of $10^{12}$ GC/kg of each of the following vectors, AAV8.TBG.PI.hPAHco.bGH, AAV8.LSP.IVS2.hPAHco.bGH, AAV8.A1AT.hPAHco.BGH, AAV8.TTR.hPAHco.BGH, AAV8.TBG.PI.hPAHnativesequence.bGH, AAV8.ABPS.TBG.hFIXintron.hPAHco.BGH, AAV8.ABPS.TBG-S1.hFIXintron.hPAHco.BGH, AAV8.ApoE.A1AT.hFIXintron.hPAHco.BGH, is also performed and served as a comparison.

In conclusion, a single injection of AAV8.TBG.PI.hPAHco.WPRE.bGH vector resulted in substantial plasma phenylalanine reduction and concomitant functional correction when administered intravenously in three PAH-deficient mice.

Example 4: AAV Gene Therapy for Phenylketonuria

Phenylketonuria (PKU) is an autosomal recessive genetic disorder caused by the attenuation of phenylalanine-4-hydroxylase (PAH) activity, resulting in the buildup of phenylalanine in the tissues and blood. High levels of phenylalanine in the bloodstream are thought to inhibit the transport of other large neutral amino acids across the blood brain barrier, affecting brain development and resulting in intellectual disability and seizures. Treatment for PKU is currently limited to maintenance of a strict phenylalanine-restricted diet and products directed at stabilizing residual PAH. A liver-targeted AAV gene therapy approach described herein is to improve upon the current standard of care.

To investigate the development of gene therapy for PKU, four unique mouse strains were created by inducing different mutations in exon 1 of the PAH gene by CRISPR/Cas9 technology as described herein. A natural history study was performed on each of these strains to determine the progression of the disease and identify the strain that best replicated the human PKU phenotype. PKU colonies, designated B and C, both contained a single base pair (bp) deletion at different locations in exon 1 and maintained average phenylalanine levels of 2049 µM and 1705 µM, respectively, compared to normal levels of 70 µM. PKU colony A, despite having a 64 bp deletion and a 3 bp insertion in exon 1 of the PAH gene, had a modestly higher average phenylalanine level of 477 µM. PKU colony D, which had a 6 bp deletion, had phenylalanine levels equivalent to wild type littermates. Following AAV8 vector administration at a dose of $1\times10^{12}$ GC/kg for expression of a human codon optimized version of PAH to the PKU B mouse colony, plasma phenylalanine levels were reduced by 87% to 222 µM. This reduction in plasma phenylalanine levels restored the ability of the males to produce offspring. These results represent development of an AAV-based therapeutic for PKU.

All publications cited in this specification are incorporated herein by reference. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

The invention claimed is:

1. A recombinant adeno-associated virus (AAV) comprising an AAV capsid and a vector genome packaged therein, said vector genome comprising:

(a) a nucleotide sequence comprising SEQ ID NO: 1 encoding a human phenylalanine hydroxylase (PAH).

2. The recombinant AAV of claim 1, wherein the vector genome further comprises:

(b) one or more copies of an enhancer sequence;

(c) a promoter sequence; and (d) a poly A sequence, wherein the nucleotide sequence encoding the PAH is operably linked to the one or more copies of an enhancer sequence and the promoter sequence.

3. The recombinant AAV of claim 2, wherein the one or more copies of an enhancer sequence is two copies of an α1-microglogubulin/bikunin precursor enhancer sequence.

4. The recombinant AAV of claim 2, wherein the promoter sequence comprises a TBG promoter sequence.

5. The recombinant AAV of claim 4, wherein the TBG promoter sequence comprises SEQ ID NO: 9.

6. The recombinant AAV of claim 2, wherein the polyA sequence is a bGH polyA sequence.

7. The recombinant AAV of claim 6, wherein the bGH polyA sequence comprises SEQ ID NO: 12.

8. The recombinant AAV of claim 2, wherein:

(i) the one or more copies of an enhancer sequence is two copies of an α1-microglogubulin/bikunin precursor enhancer sequence (ii) the promoter sequence is a TBG promoter sequence comprising SEQ ID NO: 9; and (iii) the polyA sequence is a bGH polyA sequence comprising SEQ ID NO: 12.

9. The recombinant AAV of claim 8, wherein the vector genome further comprises an AAV 5' ITR and/or an AAV3' ITR from AAV2.

10. The recombinant AAV of claim 1, wherein the vector genome further comprises an AAV 5' ITR from AAV2 and/or an AAV3' ITR from AAV2.

11. The recombinant AAV of claim 1, wherein the AAV capsid is from a clade E AAV.

12. A method of treating phenylketonuria in a patient in need thereof, the method comprising administering the recombinant AAV of claim 1 to the patient.

13. The method of claim 12, wherein about $1\times10^{10}$ to about $1\times10^{15}$ genome copies (GC)/kg of the recombinant AAV in an aqueous suspension are administered to the patient, wherein the GC are calculated as determined based on oqPCR or ddPCR.

14. The method of claim 12, wherein the recombinant AAV further comprises:

(i) two copies of an α1-microglogubulin/bikunin precursor enhancer sequence (ii) a TBG promoter sequence comprising SEQ ID NO: 9; and (iii) a bGH polyA sequence comprising SEQ ID NO: 12.

15. A plasmid comprising an expression cassette, the expression cassette comprising a nucleotide sequence comprising SEQ ID NO: 1 encoding a human phenylalanine hydroxylase (PAH).

16. The plasmid of claim 15, wherein the expression cassette further comprises two copies of an α1-microglogubulin/bikunin precursor enhancer sequence, and a bGH polyA sequence, wherein the two copies of the α1-microglogubulin/bikunin precursor enhancer sequence, the TBG promoter sequence, the nucleotide sequence encoding the PAH, and the bGH polyA sequence are operably linked.

17. The plasmid of claim 16, wherein the TBG promoter sequence comprises SEQ ID NO: 9 and/or bGH polyA sequence comprises SEQ ID NO: 12.

18. The plasmid of claim 16, wherein the expression cassette is flanked by an AAV 5' ITR from AAV2 and/or an AAV3' ITR from AAV2.

19. The plasmid of claim 18, wherein the AAV 5' ITR from AAV2 comprises SEQ ID NO: 16 and/or the AAV 3' ITR from AAV2 comprises SEQ ID NO: 17.

* * * * *